United States Patent
Phelps et al.

(10) Patent No.: US 7,101,402 B2
(45) Date of Patent: Sep. 5, 2006

(54) DESIGNS FOR LEFT VENTRICULAR CONDUIT

(75) Inventors: David Phelps, Louisville, KY (US); Greg Furnish, Louisville, KY (US); Todd Hall, Goshen, KY (US); Scott Wolf, Minneapolis, MN (US); Peter Wilk, New York, NY (US)

(73) Assignee: Percardia, Inc., Merrimack, NH (US)

( * ) Notice: Subject to any disclaimer, the term of this patent is extended or adjusted under 35 U.S.C. 154(b) by 423 days.

(21) Appl. No.: 10/456,488

(22) Filed: Jun. 9, 2003

(65) Prior Publication Data

US 2003/0195458 A1 Oct. 16, 2003

Related U.S. Application Data

(63) Continuation of application No. 09/829,449, filed on Apr. 10, 2001, now Pat. No. 6,610,100, which is a continuation of application No. 09/369,048, filed on Aug. 4, 1999, now Pat. No. 6,290,728.

(60) Provisional application No. 60/104,397, filed on Oct. 15, 1998, provisional application No. 60/099,767, filed on Sep. 10, 1998.

(51) Int. Cl.
*A61F 2/06* (2006.01)

(52) U.S. Cl. ..................... 623/23.7; 623/903

(58) Field of Classification Search ...... 623/1.15–1.16, 623/23.7, 903; 604/8; 606/108
See application file for complete search history.

(56) References Cited

U.S. PATENT DOCUMENTS

| | | | |
|---|---|---|---|
| 4,503,568 A | 3/1985 | Madras | |
| 4,733,665 A | 3/1988 | Palmaz | |
| 4,769,029 A | 9/1988 | Patel | |
| 4,953,553 A | 9/1990 | Tremulis | |
| 4,995,857 A | 2/1991 | Arnold | |
| 5,035,702 A | 7/1991 | Taheri | |
| 5,135,467 A | 8/1992 | Citron | |
| 5,193,546 A | 3/1993 | Shaknovich | |
| 5,258,008 A | 11/1993 | Wilk | |
| 5,287,861 A | 2/1994 | Wilk | |
| 5,330,486 A | 7/1994 | Wilk | |
| 5,344,426 A | 9/1994 | Lau et al. | |
| 5,385,541 A | 1/1995 | Kirsch et al. | |
| 5,389,096 A | 2/1995 | Aita et al. | |
| 5,409,019 A | 4/1995 | Wilk | |

(Continued)

FOREIGN PATENT DOCUMENTS

AU 2001281277 B2 11/2001

(Continued)

OTHER PUBLICATIONS

Anne Bohning, Kenneth Jochim & Louis N. Katz; "The Thebesian Vessels as a Source of Nourishment for the Myocardium"; American Journal of Physiology; 1933; pp. 183-200; vol. 106; American Physiological Society; U.S.A.

(Continued)

*Primary Examiner*—Suzette J-J Gherbi
(74) *Attorney, Agent, or Firm*—Finnegan, Henderson, Farabow, Garrett & Dunner, LLP

(57) ABSTRACT

A conduit is provided to provide a bypass around a blockage in the coronary artery. The conduit is adapted to be positioned in the myocardium or heart wall to provide a passage for blood to flow between a chamber of the heart such as the left ventricle and the coronary artery, distal to the blockage. The stent is self-expanding or uses a balloon to expand the stent in the heart wall. Various attachment means are provided to anchor the stent and prevent its migration.

69 Claims, 27 Drawing Sheets

U.S. PATENT DOCUMENTS

| | | |
|---|---|---|
| 5,411,552 A | 5/1995 | Andersen et al. |
| 5,423,851 A | 6/1995 | Samuels |
| 5,429,144 A | 7/1995 | Wilk |
| 5,443,497 A | 8/1995 | Venbrux |
| 5,456,712 A | 10/1995 | Maginot |
| 5,456,714 A | 10/1995 | Owen |
| 5,470,320 A | 11/1995 | Tiefenbrun et al. |
| 5,527,337 A | 6/1996 | Stack et al. |
| 5,554,119 A | 9/1996 | Harrison et al. |
| 5,578,075 A | 11/1996 | Dayton |
| 5,593,434 A | 1/1997 | Williams |
| 5,609,626 A | 3/1997 | Quijano et al. |
| 5,618,299 A | 4/1997 | Khosravi et al. |
| 5,655,548 A * | 8/1997 | Nelson et al. .............. 128/898 |
| 5,662,124 A | 9/1997 | Wilk |
| 5,733,267 A | 3/1998 | Del Toro |
| 5,755,682 A | 5/1998 | Knudson et al. |
| 5,755,781 A * | 5/1998 | Jayaraman ................ 623/1.16 |
| 5,758,663 A | 6/1998 | Wilk et al. |
| 5,797,933 A | 8/1998 | Snow et al. |
| 5,807,384 A | 9/1998 | Mueller |
| 5,824,038 A | 10/1998 | Wall |
| 5,824,071 A | 10/1998 | Nelson et al. |
| 5,830,222 A | 11/1998 | Makower |
| 5,840,081 A | 11/1998 | Andersen et al. |
| 5,843,163 A | 12/1998 | Wall |
| 5,851,232 A | 12/1998 | Lois |
| 5,855,597 A | 1/1999 | Jayaraman |
| 5,865,723 A | 2/1999 | Love |
| 5,876,373 A | 3/1999 | Giba et al. |
| 5,876,419 A | 3/1999 | Carpenter et al. |
| 5,878,751 A | 3/1999 | Hussein et al. |
| 5,885,259 A | 3/1999 | Berg |
| 5,908,028 A | 6/1999 | Wilk |
| 5,908,029 A | 6/1999 | Knudson et al. |
| 5,922,022 A | 7/1999 | Nash et al. |
| 5,925,012 A | 7/1999 | Murphy-Chutorian et al. |
| 5,931,848 A | 8/1999 | Saadat |
| 5,935,119 A | 8/1999 | Guy et al. |
| 5,935,161 A | 8/1999 | Robinson et al. |
| 5,935,162 A | 8/1999 | Dang |
| 5,938,632 A | 8/1999 | Ellis |
| 5,944,019 A | 8/1999 | Knudson et al. |
| 5,961,548 A | 10/1999 | Shmulewitz |
| 5,968,064 A | 10/1999 | Selmon et al. |
| 5,968,093 A | 10/1999 | Kranz |
| 5,971,993 A | 10/1999 | Hussein et al. |
| 5,976,155 A | 11/1999 | Foreman et al. |
| 5,976,159 A | 11/1999 | Bolduc et al. |
| 5,976,169 A | 11/1999 | Imran |
| 5,976,181 A | 11/1999 | Whelan et al. |
| 5,976,182 A | 11/1999 | Cox |
| 5,976,192 A | 11/1999 | McIntyre et al. |
| 5,976,650 A | 11/1999 | Campbell et al. |
| 5,979,455 A | 11/1999 | Maginot |
| 5,980,533 A | 11/1999 | Holman |
| 5,980,548 A | 11/1999 | Evans et al. |
| 5,980,551 A | 11/1999 | Summers et al. |
| 5,980,552 A | 11/1999 | Pinchasik et al. |
| 5,980,553 A | 11/1999 | Gray et al. |
| 5,980,566 A | 11/1999 | Alt et al. |
| 5,984,955 A | 11/1999 | Wisselink |
| 5,984,956 A | 11/1999 | Tweden et al. |
| 5,984,963 A | 11/1999 | Ryan et al. |
| 5,984,965 A | 11/1999 | Knapp et al. |
| 5,989,207 A | 11/1999 | Hughes |
| 5,989,287 A | 11/1999 | Yang et al. |
| 5,993,481 A | 11/1999 | Marcade et al. |
| 5,993,482 A | 11/1999 | Chuter |
| 5,997,525 A | 12/1999 | March et al. |
| 5,997,563 A | 12/1999 | Kretzers |
| 5,997,573 A | 12/1999 | Quijano et al. |
| 5,999,678 A | 12/1999 | Murphy-Chutorian et al. |
| 6,001,123 A | 12/1999 | Lau |
| 6,004,261 A | 12/1999 | Sinofsky et al. |
| 6,004,347 A | 12/1999 | McNamara et al. |
| 6,004,348 A | 12/1999 | Banas et al. |
| 6,007,543 A | 12/1999 | Ellis et al. |
| 6,007,544 A | 12/1999 | Kim |
| 6,007,575 A | 12/1999 | Samuels |
| 6,007,576 A | 12/1999 | McClellan |
| 6,010,449 A | 1/2000 | Selmon et al. |
| 6,010,530 A | 1/2000 | Goicoechea |
| 6,017,365 A | 1/2000 | Von Oepen |
| 6,026,814 A | 2/2000 | LaFontaine et al. |
| 6,029,672 A | 2/2000 | Vanney et al. |
| 6,035,856 A | 3/2000 | LaFontaine et al. |
| 6,036,677 A | 3/2000 | Javier, Jr. et al. |
| 6,036,697 A | 3/2000 | DiCaprio |
| 6,045,565 A | 4/2000 | Ellis et al. |
| 6,053,911 A | 4/2000 | Ryan et al. |
| 6,053,924 A | 4/2000 | Hussein |
| 6,053,942 A | 4/2000 | Eno et al. |
| 6,056,743 A | 5/2000 | Ellis et al. |
| 6,067,988 A | 5/2000 | Mueller |
| 6,068,638 A | 5/2000 | Makower |
| 6,071,292 A | 6/2000 | Makower et al. |
| 6,076,529 A | 6/2000 | Vanney et al. |
| 6,080,163 A | 6/2000 | Hussein et al. |
| 6,080,170 A | 6/2000 | Nash et al. |
| 6,092,526 A | 7/2000 | LaFontaine et al. |
| 6,093,166 A | 7/2000 | Knudson et al. |
| 6,093,177 A | 7/2000 | Javier, Jr. et al. |
| 6,093,185 A | 7/2000 | Ellis et al. |
| 6,095,997 A | 8/2000 | French et al. |
| 6,102,941 A | 8/2000 | Tweden et al. |
| 6,106,538 A | 8/2000 | Shiber |
| 6,110,201 A | 8/2000 | Quijano et al. |
| 6,113,630 A | 9/2000 | Vanney et al. |
| 6,113,823 A | 9/2000 | Eno |
| 6,120,520 A | 9/2000 | Saadat et al. |
| 6,123,682 A | 9/2000 | Knudson et al. |
| 6,126,649 A | 10/2000 | VanTassel et al. |
| 6,126,654 A | 10/2000 | Giba et al. |
| 6,132,451 A | 10/2000 | Payne et al. |
| 6,139,541 A | 10/2000 | Vanney et al. |
| 6,152,141 A | 11/2000 | Stevens et al. |
| 6,155,264 A | 12/2000 | Ressemann et al. |
| 6,156,031 A | 12/2000 | Aita et al. |
| 6,157,852 A | 12/2000 | Selmon et al. |
| 6,159,225 A | 12/2000 | Makower |
| 6,162,245 A | 12/2000 | Jayaraman |
| 6,165,185 A | 12/2000 | Shennib et al. |
| 6,165,188 A | 12/2000 | Saadat et al. |
| 6,168,614 B1 | 1/2001 | Andersen et al. |
| 6,171,251 B1 | 1/2001 | Mueller et al. |
| 6,182,668 B1 | 2/2001 | Tweden et al. |
| 6,186,972 B1 | 2/2001 | Nelson et al. |
| 6,187,034 B1 | 2/2001 | Frantzen |
| 6,190,353 B1 | 2/2001 | Makower et al. |
| 6,193,726 B1 | 2/2001 | Vanney |
| 6,193,734 B1 | 2/2001 | Bolduc et al. |
| D438,618 S | 3/2001 | Solem |
| 6,196,230 B1 | 3/2001 | Hall et al. |
| 6,197,050 B1 | 3/2001 | Eno et al. |
| 6,197,324 B1 | 3/2001 | Crittenden |
| 6,200,311 B1 | 3/2001 | Danek et al. |
| 6,203,556 B1 | 3/2001 | Evans et al. |
| 6,206,914 B1 * | 3/2001 | Soykan et al. ............. 623/1.42 |
| 6,213,126 B1 | 4/2001 | LaFontaine et al. |
| 6,214,041 B1 | 4/2001 | Tweden et al. |
| 6,217,527 B1 | 4/2001 | Selmon et al. |
| 6,217,549 B1 | 4/2001 | Selmon et al. |
| 6,217,575 B1 | 4/2001 | DeVore et al. |

| | | |
|---|---|---|
| 6,221,049 B1 | 4/2001 | Selmon et al. |
| 6,223,752 B1 | 5/2001 | Vanney et al. |
| 6,224,584 B1 | 5/2001 | March et al. |
| 6,231,546 B1 | 5/2001 | Milo et al. |
| 6,231,551 B1 | 5/2001 | Barbut |
| 6,231,587 B1 | 5/2001 | Makower |
| 6,235,000 B1 | 5/2001 | Milo et al. |
| 6,237,607 B1 | 5/2001 | Vanney et al. |
| 6,238,406 B1 | 5/2001 | Ellis et al. |
| 6,241,667 B1 | 6/2001 | Vetter et al. |
| 6,245,102 B1 | 6/2001 | Jayaraman |
| 6,248,112 B1 | 6/2001 | Gambale et al. |
| 6,250,305 B1 | 6/2001 | Tweden |
| 6,251,079 B1 | 6/2001 | Gambale et al. |
| 6,251,104 B1 | 6/2001 | Kesten et al. |
| 6,251,116 B1 | 6/2001 | Shennib et al. |
| 6,251,418 B1 | 6/2001 | Ahern et al. |
| 6,253,768 B1 | 7/2001 | Wilk |
| 6,253,769 B1 | 7/2001 | LaFontaine et al. |
| 6,254,564 B1 | 7/2001 | Wilk et al. |
| 6,258,052 B1 | 7/2001 | Milo |
| 6,258,117 B1 * | 7/2001 | Camrud et al. ............ 623/1.16 |
| 6,258,119 B1 | 7/2001 | Hussein et al. |
| 6,261,304 B1 | 7/2001 | Hall et al. |
| 6,283,951 B1 | 9/2001 | Flaherty et al. |
| 6,283,983 B1 | 9/2001 | Makower et al. |
| 6,285,903 B1 | 9/2001 | Rosenthal et al. |
| 6,287,317 B1 | 9/2001 | Makower et al. |
| 6,290,709 B1 | 9/2001 | Ellis et al. |
| 6,290,719 B1 | 9/2001 | Garberoglio |
| 6,290,728 B1 | 9/2001 | Phelps et al. |
| 6,302,875 B1 | 10/2001 | Makower et al. |
| 6,302,892 B1 | 10/2001 | Wilk |
| 6,306,125 B1 | 10/2001 | Parker et al. |
| 6,322,548 B1 | 11/2001 | Payne et al. |
| 6,330,884 B1 | 12/2001 | Kim |
| 6,344,027 B1 | 2/2002 | Goll |
| 6,350,248 B1 | 2/2002 | Knudson et al. |
| 6,352,543 B1 | 3/2002 | Cole |
| 6,361,519 B1 | 3/2002 | Knudson et al. |
| 6,363,938 B1 | 4/2002 | Saadat et al. |
| 6,363,939 B1 | 4/2002 | Wilk |
| 6,375,615 B1 | 4/2002 | Flaherty et al. |
| 6,379,319 B1 | 4/2002 | Garibotto et al. |
| 6,387,119 B1 | 5/2002 | Wolf et al. |
| 6,390,098 B1 | 5/2002 | LaFontaine et al. |
| 6,395,208 B1 | 5/2002 | Herweck et al. |
| 6,402,740 B1 | 6/2002 | Ellis et al. |
| 6,406,488 B1 | 6/2002 | Tweden et al. |
| 6,406,491 B1 | 6/2002 | Vanney |
| 6,409,697 B1 | 6/2002 | Eno et al. |
| 6,409,751 B1 | 6/2002 | Hall et al. |
| 6,416,490 B1 | 7/2002 | Ellis et al. |
| 6,423,089 B1 | 7/2002 | Gingras et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,443,158 B1 | 9/2002 | LaFontaine et al. |
| 6,447,522 B1 | 9/2002 | Gambale et al. |
| 6,447,539 B1 | 9/2002 | Nelson et al. |
| 6,454,760 B1 | 9/2002 | Vanney |
| 6,454,794 B1 | 9/2002 | Knudson et al. |
| 6,458,092 B1 | 10/2002 | Gambale et al. |
| 6,458,140 B1 | 10/2002 | Akin et al. |
| 6,458,323 B1 | 10/2002 | Boeksteger |
| 6,464,709 B1 | 10/2002 | Shennib et al. |
| 6,475,226 B1 | 11/2002 | Belef et al. |
| 6,475,244 B1 | 11/2002 | Herweck et al. |
| 6,482,220 B1 | 11/2002 | Mueller |
| 6,491,689 B1 | 12/2002 | Ellis et al. |
| 6,491,707 B1 | 12/2002 | Makower et al. |
| 6,497,722 B1 | 12/2002 | Von Oepen et al. |
| 6,506,408 B1 | 1/2003 | Palasis |
| 6,508,783 B1 | 1/2003 | DeVore |
| 6,508,824 B1 | 1/2003 | Flaherty et al. |
| 6,508,825 B1 | 1/2003 | Selmon et al. |
| 6,511,458 B1 | 1/2003 | Milo et al. |
| 6,514,217 B1 | 2/2003 | Selmon et al. |
| 6,514,271 B1 | 2/2003 | Evans et al. |
| 6,517,527 B1 | 2/2003 | Gambale et al. |
| 6,517,558 B1 | 2/2003 | Gittings et al. |
| 6,524,323 B1 | 2/2003 | Nash et al. |
| 6,524,324 B1 | 2/2003 | Mueller et al. |
| 6,530,914 B1 | 3/2003 | Mickley |
| 6,533,779 B1 | 3/2003 | Kinsella et al. |
| 6,544,220 B1 | 4/2003 | Shuman et al. |
| 6,544,230 B1 | 4/2003 | Flaherty |
| 6,559,132 B1 | 5/2003 | Holmer |
| 6,561,998 B1 | 5/2003 | Roth et al. |
| 6,562,066 B1 | 5/2003 | Martin |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,573,311 B1 | 6/2003 | Martakos et al. |
| 6,575,168 B1 | 6/2003 | LaFontaine et al. |
| 6,579,311 B1 | 6/2003 | Makower |
| 6,582,444 B1 | 6/2003 | Wilk |
| 6,582,463 B1 | 6/2003 | Mowry et al. |
| 6,585,650 B1 | 7/2003 | Solem |
| 6,587,718 B1 | 7/2003 | Talpade |
| 6,589,164 B1 | 7/2003 | Flaherty |
| 6,599,304 B1 | 7/2003 | Selmon et al. |
| 6,602,241 B1 | 8/2003 | Makower et al. |
| 6,605,053 B1 | 8/2003 | Kamm et al. |
| 6,605,113 B1 | 8/2003 | Wilk |
| 6,610,100 B1 | 8/2003 | Phelps et al. |
| 6,613,026 B1 | 9/2003 | Palasis et al. |
| 6,613,081 B1 | 9/2003 | Kim et al. |
| 6,616,626 B1 | 9/2003 | Crank et al. |
| 6,616,675 B1 | 9/2003 | Evard et al. |
| 6,632,470 B1 | 10/2003 | Morra et al. |
| 6,635,214 B1 | 10/2003 | Rapacki et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B1 | 11/2003 | Wolf et al. |
| 6,651,670 B1 | 11/2003 | Rapacki et al. |
| 6,652,540 B1 | 11/2003 | Cole et al. |
| 6,652,546 B1 | 11/2003 | Nash et al. |
| 6,655,386 B1 | 12/2003 | Makower et al. |
| 6,660,003 B1 | 12/2003 | DeVore et al. |
| 6,660,024 B1 | 12/2003 | Flaherty et al. |
| 6,666,863 B1 | 12/2003 | Wentzel et al. |
| 6,669,691 B1 | 12/2003 | Taimisto |
| 6,669,709 B1 | 12/2003 | Cohn et al. |
| 6,676,695 B1 | 1/2004 | Solem |
| 6,685,648 B1 | 2/2004 | Flaherty et al. |
| 6,685,716 B1 | 2/2004 | Flaherty et al. |
| 6,694,983 B1 | 2/2004 | Wolf et al. |
| 6,701,932 B1 | 3/2004 | Knudson et al. |
| 6,709,425 B1 | 3/2004 | Gambale et al. |
| 6,709,427 B1 | 3/2004 | Nash et al. |
| 6,709,444 B1 | 3/2004 | Makower |
| 6,719,770 B1 | 4/2004 | Laufer et al. |
| 6,719,805 B1 * | 4/2004 | Ahern .................... 623/23.74 |
| 6,726,677 B1 | 4/2004 | Flaherty et al. |
| 6,746,426 B1 | 6/2004 | Flaherty et al. |
| 6,746,464 B1 | 6/2004 | Makower |
| 6,748,258 B1 | 6/2004 | Mueller et al. |
| 6,774,155 B1 | 8/2004 | Martakos et al. |
| 6,774,278 B1 | 8/2004 | Ragheb et al. |
| 6,786,929 B1 | 9/2004 | Gambale et al. |
| 6,802,858 B1 | 10/2004 | Gambale et al. |
| 6,808,498 B1 | 10/2004 | Laroya et al. |

| | | |
|---|---|---|
| 6,808,504 B1 | 10/2004 | Schorgl et al. |
| 6,830,568 B1 | 12/2004 | Kesten et al. |
| 6,854,467 B1 | 2/2005 | Boekstegers |
| 6,855,160 B1 | 2/2005 | Gambale et al. |
| 6,863,684 B1 | 3/2005 | Kim et al. |
| 6,878,371 B1 | 4/2005 | Ueno et al. |
| 6,881,199 B1 | 4/2005 | Wilk et al. |
| 6,890,463 B1 | 5/2005 | Martakos et al. |
| 6,893,413 B1 | 5/2005 | Martin |
| 6,913,021 B1 | 7/2005 | Knudson et al. |
| 6,916,304 B1 | 7/2005 | Eno et al. |
| 6,926,690 B1 | 8/2005 | Renati |
| 6,929,009 B1 | 8/2005 | Makower et al. |
| 6,929,011 B1 | 8/2005 | Knudson et al. |
| 6,945,949 B1 | 9/2005 | Wilk |
| 6,949,080 B1 | 9/2005 | Wolf et al. |
| 6,949,118 B1 | 9/2005 | Kohler et al. |
| 6,953,476 B1 | 10/2005 | Shalev |
| 6,953,481 B1 | 10/2005 | Phelps et al. |
| 6,955,681 B1 | 10/2005 | Evans et al. |
| 2001/0000041 A1 | 3/2001 | Selmon et al. |
| 2001/0003985 A1 | 6/2001 | LaFontaine et al. |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0008969 A1 | 7/2001 | Evans et al. |
| 2001/0012924 A1 | 8/2001 | Milo et al. |
| 2001/0012948 A1 | 8/2001 | Vanney |
| 2001/0014813 A1 | 8/2001 | Saadat et al. |
| 2001/0016700 A1 | 8/2001 | Eno et al. |
| 2001/0018596 A1 | 8/2001 | Selmon et al. |
| 2001/0020172 A1 | 9/2001 | Selmon et al. |
| 2001/0025643 A1 | 10/2001 | Foley |
| 2001/0027287 A1 | 10/2001 | Shmulewitz et al. |
| 2001/0029385 A1 | 10/2001 | Shennib et al. |
| 2001/0034547 A1 | 10/2001 | Hall et al. |
| 2001/0037117 A1 | 11/2001 | Gambale et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0041902 A1 | 11/2001 | Lepulu et al. |
| 2001/0044631 A1 | 11/2001 | Akin et al. |
| 2001/0047165 A1 | 11/2001 | Makower et al. |
| 2001/0047197 A1 | 11/2001 | Foley |
| 2001/0049523 A1 | 12/2001 | DeVore et al. |
| 2001/0053932 A1 | 12/2001 | Phelps et al. |
| 2002/0002349 A1 | 1/2002 | Flaherty et al. |
| 2002/0004662 A1 | 1/2002 | Wilk |
| 2002/0004663 A1 | 1/2002 | Gittings et al. |
| 2002/0007138 A1 | 1/2002 | Wilk et al. |
| 2002/0029079 A1 | 3/2002 | Kim et al. |
| 2002/0032476 A1 | 3/2002 | Gambale et al. |
| 2002/0032478 A1 | 3/2002 | Boekstegers et al. |
| 2002/0033180 A1 | 3/2002 | Solem |
| 2002/0045928 A1 | 4/2002 | Boekstegers |
| 2002/0049486 A1 | 4/2002 | Knudson et al. |
| 2002/0049495 A1 | 4/2002 | Kutryk et al. |
| 2002/0058897 A1 | 5/2002 | Renati |
| 2002/0062146 A1 | 5/2002 | Makower et al. |
| 2002/0065478 A1 | 5/2002 | Knudson et al. |
| 2002/0072699 A1 | 6/2002 | Knudson et al. |
| 2002/0072758 A1 | 6/2002 | Reo et al. |
| 2002/0077566 A1 | 6/2002 | Laroya et al. |
| 2002/0077654 A1 | 6/2002 | Javier, Jr. et al. |
| 2002/0082546 A1 | 6/2002 | Crank et al. |
| 2002/0092535 A1 | 7/2002 | Wilk |
| 2002/0092536 A1 | 7/2002 | LaFontaine et al. |
| 2002/0095110 A1 | 7/2002 | Vanney et al. |
| 2002/0095111 A1 | 7/2002 | Tweden et al. |
| 2002/0095206 A1 | 7/2002 | Addonizio et al. |
| 2002/0099392 A1 | 7/2002 | Mowry et al. |
| 2002/0099404 A1 | 7/2002 | Mowry |
| 2002/0100484 A1 | 8/2002 | Hall et al. |
| 2002/0103459 A1 | 8/2002 | Sparks et al. |
| 2002/0103495 A1 | 8/2002 | Cole |
| 2002/0103534 A1 | 8/2002 | Vanney et al. |
| 2002/0111644 A1 | 8/2002 | Shuman et al. |
| 2002/0111672 A1 | 8/2002 | Kim et al. |
| 2002/0123698 A1 | 9/2002 | Garibotto et al. |
| 2002/0123786 A1 | 9/2002 | Gittings et al. |
| 2002/0138087 A1 | 9/2002 | Shennib et al. |
| 2002/0143285 A1 | 10/2002 | Eno et al. |
| 2002/0143289 A1 | 10/2002 | Ellis et al. |
| 2002/0143347 A1 | 10/2002 | Cole et al. |
| 2002/0144696 A1 | 10/2002 | Sharkawy et al. |
| 2002/0161383 A1 | 10/2002 | Akin et al. |
| 2002/0161424 A1 | 10/2002 | Rapacki et al. |
| 2002/0165479 A1 | 11/2002 | Wilk |
| 2002/0165606 A1 | 11/2002 | Wolf et al. |
| 2002/0179098 A1 | 12/2002 | Makower et al. |
| 2002/0183716 A1 | 12/2002 | Herweck et al. |
| 2002/0193782 A1 | 12/2002 | Ellis et al. |
| 2003/0015816 A1 | 1/2003 | Rapacki et al. |
| 2003/0018379 A1 | 1/2003 | Knudson et al. |
| 2003/0044315 A1 | 3/2003 | Boekstegers |
| 2003/0045828 A1 | 3/2003 | Wilk |
| 2003/0055371 A1 | 3/2003 | Wolf et al. |
| 2003/0062650 A1 | 4/2003 | Martakos et al. |
| 2003/0069532 A1 | 4/2003 | Mowry et al. |
| 2003/0069587 A1 | 4/2003 | Schorgl et al. |
| 2003/0073973 A1 | 4/2003 | Evans et al. |
| 2003/0074006 A1 | 4/2003 | Mowry et al. |
| 2003/0078561 A1 | 4/2003 | Gambale et al. |
| 2003/0078562 A1 | 4/2003 | Makower et al. |
| 2003/0083678 A1 | 5/2003 | Herweck et al. |
| 2003/0097172 A1 | 5/2003 | Shalev et al. |
| 2003/0100920 A1 | 5/2003 | Akin et al. |
| 2003/0105514 A1 | 6/2003 | Phelps et al. |
| 2003/0114872 A1 | 6/2003 | Mueller et al. |
| 2003/0120195 A1 | 6/2003 | Milo et al. |
| 2003/0120259 A1 | 6/2003 | Mickley |
| 2003/0125798 A1 | 7/2003 | Martin |
| 2003/0130611 A1 | 7/2003 | Martin |
| 2003/0130719 A1 | 7/2003 | Martin |
| 2003/0135260 A1 | 7/2003 | Kohler et al. |
| 2003/0149126 A1 | 8/2003 | Martakos et al. |
| 2003/0149474 A1 | 8/2003 | Becker |
| 2003/0153901 A1 | 8/2003 | Herweck et al. |
| 2003/0158509 A1 | 8/2003 | Tweden et al. |
| 2003/0158573 A1 | 8/2003 | Gittings et al. |
| 2003/0163198 A1 | 8/2003 | Morra et al. |
| 2003/0171800 A1 | 9/2003 | Bicek et al. |
| 2003/0181938 A1 | 9/2003 | Roth et al. |
| 2003/0191449 A1 | 10/2003 | Nash et al. |
| 2003/0195457 A1 | 10/2003 | LaFontaine et al. |
| 2003/0195458 A1 | 10/2003 | Phelps et al. |
| 2003/0195606 A1 | 10/2003 | Davidson et al. |
| 2003/0204160 A1 | 10/2003 | Kamm et al. |
| 2003/0212413 A1 | 11/2003 | Wilk |
| 2003/0216678 A1 | 11/2003 | March et al. |
| 2003/0216679 A1 | 11/2003 | Wolf et al. |
| 2003/0216801 A1 | 11/2003 | Tweden et al. |
| 2003/0220661 A1 | 11/2003 | Mowry et al. |
| 2003/0225425 A1 | 12/2003 | Kupiecki et al. |
| 2003/0229366 A1 | 12/2003 | Reggie et al. |
| 2003/0236542 A1 | 12/2003 | Makower |
| 2004/0006298 A1 | 1/2004 | Wilk |
| 2004/0006301 A1 | 1/2004 | Sell et al. |
| 2004/0015193 A1 | 1/2004 | Lamson et al. |
| 2004/0015225 A1 | 1/2004 | Kim et al. |
| 2004/0019348 A1 | 1/2004 | Stevens et al. |
| 2004/0037946 A1 | 2/2004 | Morra et al. |
| 2004/0044392 A1 | 3/2004 | Von Oepen |
| 2004/0049171 A1 | 3/2004 | Mowry et al. |
| 2004/0058097 A1 | 3/2004 | Weder |
| 2004/0059280 A1 | 3/2004 | Makower et al. |

| | | | | | | |
|---|---|---|---|---|---|---|
| 2004/0073157 A1 | 4/2004 | Knudson et al. | | EP | 0 792 624 A1 | 9/1997 |
| 2004/0073238 A1 | 4/2004 | Makower | | EP | 0 797 957 A1 | 10/1997 |
| 2004/0077987 A1 | 4/2004 | Rapacki et al. | | EP | 0 797 958 A1 | 10/1997 |
| 2004/0077988 A1 | 4/2004 | Tweden et al. | | EP | 0 799 604 A1 | 10/1997 |
| 2004/0077990 A1 | 4/2004 | Knudson et al. | | EP | 0 801 928 A1 | 10/1997 |
| 2004/0088042 A1 | 5/2004 | Kim et al. | | EP | 0 815 798 A2 | 1/1998 |
| 2004/0102830 A1 | 5/2004 | Williams | | EP | 0 824 903 A1 | 2/1998 |
| 2004/0106931 A1 | 6/2004 | Guiles et al. | | EP | 0 829 239 A1 | 3/1998 |
| 2004/0113306 A1 | 6/2004 | Rapacki et al. | | EP | 0 836 834 A2 | 4/1998 |
| 2004/0116999 A1 | 6/2004 | Ledergerber | | EP | 0 953 921 A2 | 7/1998 |
| 2004/0118415 A1 | 6/2004 | Hall et al. | | EP | 0 858 779 A1 | 8/1998 |
| 2004/0122318 A1 | 6/2004 | Flaherty et al. | | EP | 0 876 796 A2 | 11/1998 |
| 2004/0122347 A1 | 6/2004 | Knudson et al. | | EP | 0 876 803 A2 | 11/1998 |
| 2004/0133154 A1 | 7/2004 | Flaherty et al. | | EP | 0 888 750 A1 | 1/1999 |
| 2004/0133225 A1 | 7/2004 | Makower | | EP | 0 895 752 A1 | 2/1999 |
| 2004/0138562 A1 | 7/2004 | Makower et al. | | EP | 0 903 123 A2 | 3/1999 |
| 2004/0147837 A1 | 7/2004 | Mccauley et al. | | EP | 0 904 745 A2 | 3/1999 |
| 2004/0147868 A1 | 7/2004 | Bardsley et al. | | EP | 0 934 728 A2 | 8/1999 |
| 2004/0147869 A1 | 7/2004 | Wolf et al. | | EP | 0 955-017 A2 | 11/1999 |
| 2004/0158143 A1 | 8/2004 | Flaherty et al. | | EP | 0 955 019 A2 | 11/1999 |
| 2004/0158227 A1 | 8/2004 | Nash et al. | | EP | 0 962 194 | 12/1999 |
| 2004/0162608 A1 | 8/2004 | Haverich | | EP | 1 020 166 A1 | 7/2000 |
| 2004/0167444 A1 | 8/2004 | Laroya et al. | | EP | 1 027 870 A1 | 8/2000 |
| 2004/0168691 A1 | 9/2004 | Sharkawy et al. | | EP | 1 088 564 A1 | 4/2001 |
| 2004/0186507 A1 | 9/2004 | Hall et al. | | EP | 1 097 676 A1 | 5/2001 |
| 2004/0186557 A1 | 9/2004 | Gambale et al. | | EP | 1 166 721 A2 | 1/2002 |
| 2004/0186587 A1 | 9/2004 | Ahem | | EP | 0 959 815 A1 | 12/2002 |
| 2004/0210190 A1 | 10/2004 | Kohler et al. | | EP | 1 112 097 A1 | 6/2003 |
| 2004/0210304 A1 | 10/2004 | Seguin et al. | | EP | 0 954 248 B1 | 9/2004 |
| 2004/0215220 A1 | 10/2004 | Dolan et al. | | EP | 1 115 452 B1 | 11/2004 |
| 2004/0219180 A1 | 11/2004 | Gambale et al. | | EP | 1 477 202 A2 | 11/2004 |
| 2004/0220598 A1 | 11/2004 | Bolduc et al. | | EP | 1 107 710 B1 | 12/2004 |
| 2004/0225355 A1 | 11/2004 | Stevens | | EP | 1 484 081 A1 | 12/2004 |
| 2004/0232587 A1 | 11/2004 | Martakos et al. | | EP | 1 143 879 B1 | 3/2005 |
| 2004/0236278 A1 | 11/2004 | Herweck et al. | | EP | 1 516 599 A2 | 3/2005 |
| 2004/0236279 A1 | 11/2004 | Herweck et al. | | EP | 1 522 278 A1 | 4/2005 |
| 2004/0236410 A1 | 11/2004 | Herweck et al. | | EP | 1 547 533 A2 | 6/2005 |
| 2004/0236418 A1 | 11/2004 | Stevens | | EP | 1 027 013 B1 | 8/2005 |
| 2004/0243219 A1 | 12/2004 | Fischer et al. | | EP | 1 067 869 B1 | 11/2005 |
| 2004/0254451 A1 | 12/2004 | Mueller et al. | | GB | 2 316 322 B | 10/1998 |
| 2004/0254518 A1 | 12/2004 | Lee | | WO | WO 94/16629 A1 | 8/1994 |
| 2005/0004505 A1 | 1/2005 | Phelps et al. | | WO | WO 96/32972 A1 | 10/1996 |
| 2005/0004558 A1 | 1/2005 | Gambale et al. | | WO | WO 96/35469 A1 | 11/1996 |
| 2005/0004648 A1 | 1/2005 | Boekstegers | | WO | WO 96/39962 A1 | 12/1996 |
| 2005/0033220 A1 | 2/2005 | Wilk et al. | | WO | WO 96/39964 A1 | 12/1996 |
| 2005/0043781 A1 | 2/2005 | Foley | | WO | WO 96/39965 A1 | 12/1996 |
| 2005/0055081 A1 | 3/2005 | Goodwin et al. | | WO | WO 97/13463 A1 | 4/1997 |
| 2005/0055082 A1 | 3/2005 | Ben Muvhar et al. | | WO | WO 97/13471 A1 | 4/1997 |
| 2005/0060019 A1 | 3/2005 | Gambale et al. | | WO | WO 97/18768 A1 | 5/1997 |
| 2005/0090748 A1 | 4/2005 | Makower et al. | | WO | WO 97/27893 A1 | 8/1997 |
| 2005/0101902 A1 | 5/2005 | Navia et al. | | WO | WO 97/27897 A1 | 8/1997 |
| 2005/0101903 A1 | 5/2005 | Kohler et al. | | WO | WO 97/27898 A1 | 8/1997 |
| 2005/0101904 A1 | 5/2005 | Wilk | | WO | WO 97/32551 A1 | 9/1997 |
| 2005/0119731 A1 | 6/2005 | Brucker et al. | | WO | WO 97/41916 A1 | 11/1997 |
| 2005/0159726 A1 | 7/2005 | Evans et al. | | WO | WO 97/43961 A1 | 11/1997 |
| | | | | WO | WO 98/02099 A1 | 1/1998 |
| | FOREIGN PATENT DOCUMENTS | | | WO | WO 98/03118 A1 | 1/1998 |
| | | | | WO | WO 98/06356 A1 | 2/1998 |
| AU | 757647 B2 | 2/2003 | | WO | WO 98/08456 A1 | 3/1998 |
| AU | 776895 B2 | 9/2004 | | WO | WO 98/10714 A1 | 3/1998 |
| AU | 777443 B2 | 10/2004 | | WO | WO 98/16161 A1 | 4/1998 |
| AU | 778831 B2 | 12/2004 | | WO | WO 98/19607 A1 | 5/1998 |
| AU | 2004231189 A1 | 12/2004 | | WO | WO 98/24373 A1 | 6/1998 |
| AU | 2004242527 A1 | 1/2005 | | WO | WO 98/25533 A1 | 6/1998 |
| CA | 2378589 A1 | 2/2001 | | WO | WO 98/38916 A1 | 9/1998 |
| CA | 2381192 A1 | 2/2001 | | WO | WO 98/38925 A1 | 9/1998 |
| CA | 2385662 A1 | 3/2001 | | WO | WO 98/38939 A1 | 9/1998 |
| CA | 2407987 A1 | 11/2001 | | WO | WO 98/38941 A1 | 9/1998 |
| CA | 2418958 A1 | 2/2002 | | WO | WO 98/39038 A1 | 9/1998 |
| CA | 2435962 A1 | 8/2002 | | WO | WO 98/44869 A1 | 10/1998 |
| CA | 2457755 A1 | 2/2003 | | WO | WO 98/46115 A2 | 10/1998 |
| EP | 0 592 410 B1 | 10/1995 | | WO | WO 98/46119 A1 | 10/1998 |
| EP | 0 732 088 A2 | 9/1996 | | WO | WO 98/49964 A1 | 11/1998 |

| | | | | | | |
|---|---|---|---|---|---|---|
| WO | WO 98/53759 | A2 | 12/1998 | WO | WO 00/54661 A1 | 9/2000 |
| WO | WO 98/55027 | A2 | 12/1998 | WO | WO 00/56224 A1 | 9/2000 |
| WO | WO 98/57590 | A1 | 12/1998 | WO | WO 00/56225 A1 | 9/2000 |
| WO | WO 98/57591 | A1 | 12/1998 | WO | WO 00/56387 A1 | 9/2000 |
| WO | WO 98/57592 | A1 | 12/1998 | WO | WO 00/66007 A1 | 11/2000 |
| WO | WO 99/07296 | A1 | 2/1999 | WO | WO 00/66009 A1 | 11/2000 |
| WO | WO 99/08624 | A1 | 2/1999 | WO | WO 00/66035 A1 | 11/2000 |
| WO | WO 99/15220 | A1 | 4/1999 | WO | WO 00/69345 A1 | 11/2000 |
| WO | WO 99/17671 | A1 | 4/1999 | WO | WO 00/69504 A1 | 11/2000 |
| WO | WO 99/17683 | A1 | 4/1999 | WO | WO 00/71195 A1 | 11/2000 |
| WO | WO 99/21490 | A1 | 5/1999 | WO | WO 01/08566 A1 | 2/2001 |
| WO | WO 99/21510 | A1 | 5/1999 | WO | WO 01/08602 A1 | 2/2001 |
| WO | WO 99/22655 | A1 | 5/1999 | WO | WO 01/10340 A1 | 2/2001 |
| WO | WO 99/22658 | A1 | 5/1999 | WO | WO 01/10341 A2 | 2/2001 |
| WO | WO 99/25273 | A1 | 5/1999 | WO | WO 01/10347 A1 | 2/2001 |
| WO | WO 99/27985 | A1 | 6/1999 | WO | WO 01/10348 A1 | 2/2001 |
| WO | WO 99/32051 | A1 | 7/1999 | WO | WO 01/10349 A1 | 2/2001 |
| WO | WO 99/35977 | A1 | 7/1999 | WO | WO 01/10350 A1 | 2/2001 |
| WO | WO 99/35979 | A1 | 7/1999 | WO | WO 01/17440 A1 | 3/2001 |
| WO | WO 99/35980 | A1 | 7/1999 | WO | WO 01/17456 A1 | 3/2001 |
| WO | WO 99/36000 | A1 | 7/1999 | WO | WO 01/23016 A1 | 4/2001 |
| WO | WO 99/36001 | A1 | 7/1999 | WO | WO 01/26562 A1 | 4/2001 |
| WO | WO 99/37218 | A1 | 7/1999 | WO | WO 01/41657 A1 | 6/2001 |
| WO | WO 99/38459 | A2 | 8/1999 | WO | WO 01/49187 A1 | 7/2001 |
| WO | WO 99/38549 | A1 | 8/1999 | WO | WO 01/54652 A2 | 8/2001 |
| WO | WO 99/40853 | A1 | 8/1999 | WO | WO 01/68158 A1 | 9/2001 |
| WO | WO 99/40868 | A1 | 8/1999 | WO | WO 01/70133 A2 | 9/2001 |
| WO | WO 99/40963 | A1 | 8/1999 | WO | WO 01/72239 A2 | 10/2001 |
| WO | WO 99/44524 | A2 | 9/1999 | WO | WO 01/78801 A2 | 10/2001 |
| WO | WO 99/47071 | A1 | 9/1999 | WO | WO 01/82803 A1 | 11/2001 |
| WO | WO 99/47078 | A1 | 9/1999 | WO | WO 01/82837 A2 | 11/2001 |
| WO | WO 99/48427 | A1 | 9/1999 | WO | WO 02/011647 A2 | 2/2002 |
| WO | WO 99/48545 | A1 | 9/1999 | WO | WO 02/011807 A2 | 2/2002 |
| WO | WO 99/48549 | A2 | 9/1999 | WO | WO 02/013698 A1 | 2/2002 |
| WO | WO 99/49793 | A1 | 10/1999 | WO | WO 02/013699 A1 | 2/2002 |
| WO | WO 99/49910 | A2 | 10/1999 | WO | WO 02/013703 A1 | 2/2002 |
| WO | WO 99/51162 | A1 | 10/1999 | WO | WO 02/013704 A1 | 2/2002 |
| WO | WO 99/53863 | A1 | 10/1999 | WO | WO 02/024108 A2 | 3/2002 |
| WO | WO 99/55406 | A1 | 11/1999 | WO | WO 02/024247 A1 | 3/2002 |
| WO | WO 99/60941 | A1 | 12/1999 | WO | WO 02/024248 A1 | 3/2002 |
| WO | WO 99/62430 | A1 | 12/1999 | WO | WO 02/026310 A1 | 4/2002 |
| WO | WO 00/09195 | A1 | 2/2000 | WO | WO 02/026462 A1 | 4/2002 |
| WO | WO 00/10623 | A1 | 3/2000 | WO | WO 02/030325 A2 | 4/2002 |
| WO | WO 00/12029 | A1 | 3/2000 | WO | WO 02/030326 A2 | 4/2002 |
| WO | WO 00/13722 | A1 | 3/2000 | WO | WO 02/030330 A2 | 4/2002 |
| WO | WO 00/15146 | A1 | 3/2000 | WO | WO 02/032330 A2 | 4/2002 |
| WO | WO 00/15147 | A1 | 3/2000 | WO | WO 02/034323 A2 | 5/2002 |
| WO | WO 00/15148 | A1 | 3/2000 | WO | WO 02/045598 A2 | 6/2002 |
| WO | WO 00/15149 | A1 | 3/2000 | WO | WO 02/049465 A2 | 6/2002 |
| WO | WO 00/15275 | A2 | 3/2000 | WO | WO 02/056937 A2 | 7/2002 |
| WO | WO 00/16848 | A1 | 3/2000 | WO | WO 02/058567 A2 | 8/2002 |
| WO | WO 00/18302 | A2 | 4/2000 | WO | WO 02/058591 A2 | 8/2002 |
| WO | WO 00/18323 | A2 | 4/2000 | WO | WO 02/060509 A1 | 8/2002 |
| WO | WO 00/18325 | A1 | 4/2000 | WO | WO 02/062265 A2 | 8/2002 |
| WO | WO 00/18326 | A1 | 4/2000 | WO | WO 02/064020 A2 | 8/2002 |
| WO | WO 00/18331 | A2 | 4/2000 | WO | WO 02/071974 A2 | 9/2002 |
| WO | WO 00/18462 | A2 | 4/2000 | WO | WO 02/074175 A2 | 9/2002 |
| WO | WO 00/21436 | A1 | 4/2000 | WO | WO 02/091958 A1 | 11/2002 |
| WO | WO 00/21461 | A2 | 4/2000 | WO | WO 03/008005 A2 | 1/2003 |
| WO | WO 00/21463 | A1 | 4/2000 | WO | WO 03/015638 A2 | 2/2003 |
| WO | WO 00/24449 | A1 | 5/2000 | WO | WO 03/017870 A1 | 3/2003 |
| WO | WO 00/33725 | A2 | 6/2000 | WO | WO 03/024307 A2 | 3/2003 |
| WO | WO 00/35376 | A1 | 6/2000 | WO | WO 03/028522 A2 | 4/2003 |
| WO | WO 00/36997 | A1 | 6/2000 | WO | WO 03/030744 A1 | 4/2003 |
| WO | WO 00/41632 | A1 | 7/2000 | WO | WO 03/030784 A1 | 4/2003 |
| WO | WO 00/41633 | A1 | 7/2000 | WO | WO 03/041469 A2 | 5/2003 |
| WO | WO 00/43051 | A1 | 7/2000 | WO | WO 03/079932 A2 | 10/2003 |
| WO | WO 00/45711 | A1 | 8/2000 | WO | WO 2004/000170 A1 | 12/2003 |
| WO | WO 00/45886 | A2 | 8/2000 | WO | WO 2004/014257 A1 | 2/2004 |
| WO | WO 00/49952 | A1 | 8/2000 | WO | WO 2004/014474 A1 | 2/2004 |
| WO | WO 00/49954 | A2 | 8/2000 | WO | WO 2004/047913 A1 | 6/2004 |
| WO | WO 00/49956 | A1 | 8/2000 | WO | WO 2004/058097 A2 | 7/2004 |
| WO | WO 00/54660 | A1 | 9/2000 | | | |

WO  WO 2004/075951 A1  9/2004

OTHER PUBLICATIONS

Alfred Goldman, Seymour M. Greenstone, Fred S. Preuss, Sherman H. Strauss & En-Shu Chang; "Experimental Methods for Producing a Collateral Circulation to the Heart Directly from the Left Ventricle"; Journal of Thoracic Surgery; Mar. 1956; pp. 364-374; vol. 31, No. 3; U.S.A.

C. Massimo & L. Boffi; "Myocardial, Revascularization by a New Method of Carrying Blood Directly From the Left Ventricular Cavity into the Coronary Circulation"; Journal of Thoracic Surgery; Aug. 1957; pp. 257-264; vol. 34; U.S.A.

Banning G. Lary & Roger W. Sherman; "A method for creating a coronary-myocardial artery"; Surgery; Jun. 1966; pp. 1061-1064; vol. 59, No. 6; The C.V. Mosby Company; St. Louis, MO.

Akio Wakayabashi, Solomon T. Little, Jr. & John E. Connolly; "Myocardial Boring for the Ischemic Heart"; Archives of Surgery; Nov. 1967; pp. 743-752; vol. 95; American Medical Asssociation; U.S.A.

Julio C. Palmaz, Francisco Garcia, Randy R. Sibbitt, Fremin O. Tio, David T. Kopp, Wayne Schwesinger, Jack L. Lancaster & Peter Chang; "Expandable Intrahepatic Portacaval Shunt Stents in Dogs with Chronic Portal Hypertension"; American Journal of Roentgenology; Dec. 1986; pp. 1251-1254; vol. 147; The American Roentgen Ray Society; U.S.A.

Banning G. Lary, Antonio Camelo, Roger W. Sherman & Thomas J. Noto; "Myocardial Revascularization Experiments Using the Epicardium"; Archives of Surgery.; Jan. 1969; pp. 69-72; vol. 98; American Medical Association; U.S.A.

Ladislav Kuzela & George E. Miller, Jr.; "Experimental evaluation of direct transventricular revascularization"; Journal of Thoracic and Cardiovascular Surgery; Jun. 1969; pp. 770-773; vol. 57, No. 6; The C.V. Mosby Company; St. Louis, MO.

Ian Munro & Peter Allen; "The possibility of myocardial revascularization by creation of a left ventriculocoronary artery fistula"; The Journal of Thoracic and Cardiovascular Surgery; Jul. 1969; pp. 25-32; vol. 58, No. 1; The C.V. Mosby Company; St. Louis, MO.

Isam N. Anabtawi, Hubert F. Reigler, & Robert G. Ellison;"Experimental evaluation of myocardial tunnelization as a method of myocardial revascularization"; Journal of Thoracic and Cardiovascular Surgery; Nov. 1969; pp. 638-646; vol. 58, No. 5; The C.V. Mosby Company; St. Louis, MO.

Robert J. Gardner, Benjamin L. Plybon & Herbert E. Warden; "An Experimental Anatomic Study of Indirect Myocardial Revascularization"; Journal of Surgical Research; 1971; pp. 243-247; vol. 11; Academic Press; U.S.A.

Frank M. Galioto, Milton J. Reitman, Arnold J. Slovis & Irving A. Sarot; "Right coronary artery to left ventricle fistula: A case report and discussion"; American Heart Journal; Jul. 1971; pp. 93-97; vol. 82, No. 1; The C.V. Mosby Company; St. Louis, MO.

Joseph P. Archie Jr.; "Intramyocardial Pressure: Effect of Preload on Transmural Distribution of Systotic Coronary Blood Flow"; The American Journal of Cardiology; Jun. 1975; pp. 904-911; vol. 35; U.S.A.

L. Levinsky, T.Z. Lajos, A.B. Lee, Jr., C. Espersen, & G. Schimert; "The Revival of the Horseshoe Graft (Side-toSide Saphenous-Vein-to-Aorta Anastomosis"; The Thoracic and Cardiovascular Surgeon; Oct. 1979; pp. 322-324; vol. 27, No. 5; Georg Thieme Publishers; Stuttgart, Germany.

S. Sultan Ahmed, Bunyad Haider & Timothy J. Regan; "Silent left coronary artery-cameral fistula: probable cause of myocardial ischemia"; American Heart Journal; Oct. 1982; pp. 869-870; vol. 104, No. 4, pt. 1; The C.V. Mosby Company; St. Louis, MO.

Garrett Lee, Richard M. Ikeda, Jerold Theis, Daniel Stobbe, Claire Ogata, Henry Lui, Robert L. Reis, & Dean T. Mason; "Effects of laser Irradiation delivered by flexible fiberoptic system on the left ventricular internal myocardium"; American Heart Journal; Sep. 1983; pp. 587-590; vol. 106, No. 3; The C.V. Mosby Company; St. Louis, MO.

Julio C. Palmaz, Randy R. Sibbitt, Stewart R. Reuter, Francisco Garcia & Fremin O. Tio; "Expandable Intrahepatic Portacaval Shunt Stents: Early Experience in the Dog"; American Journal of Roentgenology; Oct. 1985; pp. 821-825; vol. 145; The American Roentgen Ray Society; U.S.A.

Goetz M. Richter, Gerd Noeldge, Julio C. Palmaz, Martin Roessle, Volker Slegerstetter, Martina Franke, Wolfgang Gerok, Werner Wenz & Edward Farthman; "Transjugular Intrahepatic Portacaval Stent Shunt: Preliminary Clinical Results"; Radiology; Mar. 1990; pp. 1027-1030; vol. 174, No. 3, Pt. 2; The Radiological Society of North America; Oak Brook, IL.

Gerald Zemel, Barry T. Katzen, Gary J. Becker, James F. Benenati & D. Skip Sallee; "Percutaneous Transjugular Portosystem Shunt"; The Journal of the American Medical Association; Jul. 1991; pp. 390-393; vol. 266, No. 3; American Medical Association; U.S.A.

Medical Industry Today Headline News; "Eclipse Gets OK to Pump Catheter Marketing in Europe"; Jul. 17, 1998; pp. 1-2; Article #07179802, Article is 349 words long; Medical Data International, Inc.; Santa Ana, CA.

Medical Industry Today Headline News; "Sales Dive, Losses Soar in 2Q for CardioGenesis"; Jul. 17, 1998; pp. 1-2; Article #07179808, Article is 560 words long; Medical Data International, Inc.; U.S.A.

Howard A. Cohen & Marco Zenati; "Alternative Approaches to Coronary Revascularization"; Current International Cardiology Reports; 1998; pp. 138-146; vol. 1; Current Science, Inc.; U.S.A.

Katherine S. Tweden, Frazier Eales, J. Douglas Cameron, Jerry C. Griffin, Eric E. Solien & Mark B. Knudson; "Ventriculocoronary Artery Bypass (VCAB), a Novel Approach to Myocardial Revascularization"; Feb. 2000; Article #2000-4653.

Stephen N. Oesterle, Nicolaus Reifart, Motoya Hayase, Eugen Haputmann, Reginald Low, Raimund Erbel, Michael Hause, Olaf Dirsch, Gerhard C. Schuler, Renu Virmani & Alan C. Yeung; "Catheter-Based Coronary Bypass: A Development Update"; Catheterization and Cardiovascular Interventions; 2003; pp. 212. 218; vol. 58; Wiley-Liss, Inc.; U.S.A.

Burch et al., "Surgical closure of coronary artery fistula emptying into left ventricle," American Heart Journal, Jan. 1980, vol. 99, No. 1, p. 133.

US 6,331,185, 12/2001, Gambale et al. (withdrawn)

* cited by examiner

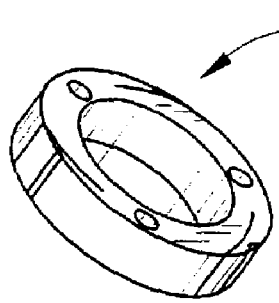
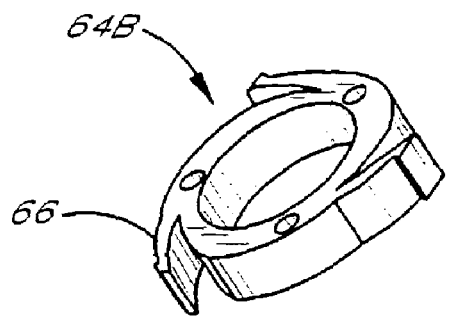
FIG. 22    FIG. 23
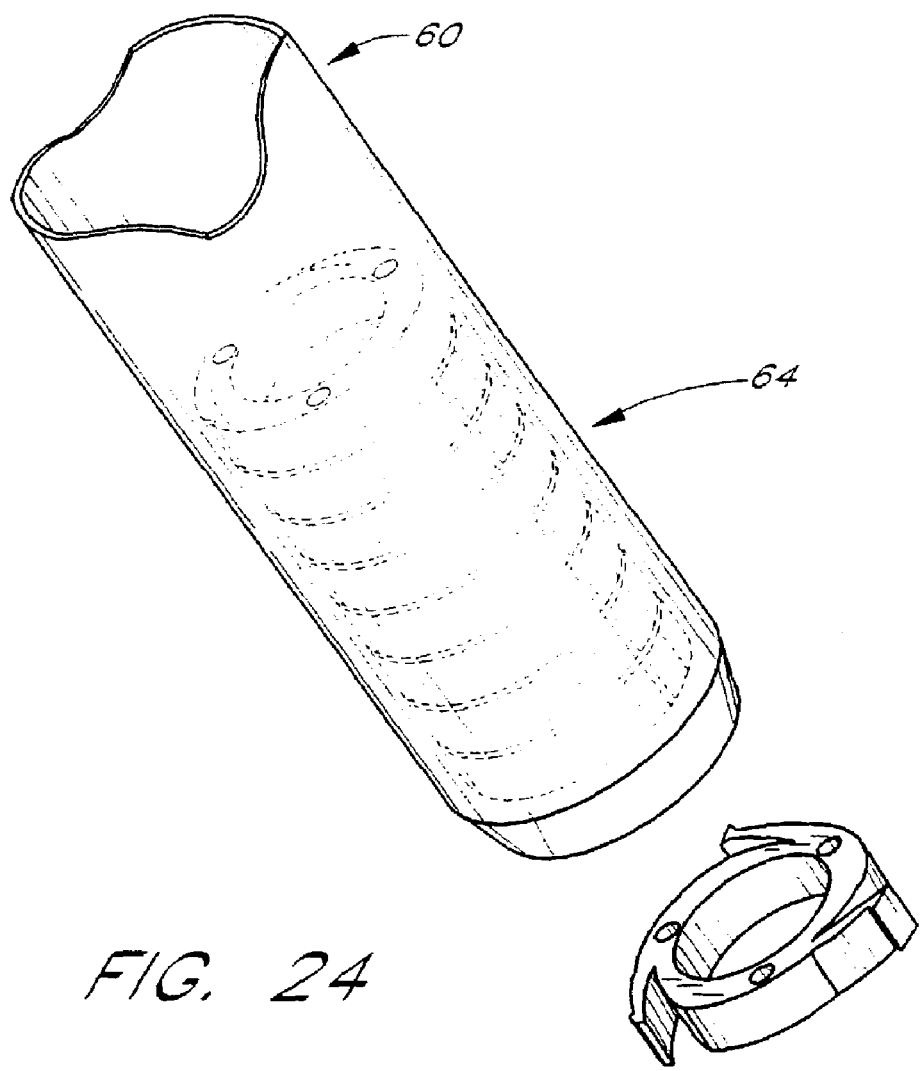
FIG. 24

DESIGNS FOR LEFT VENTRICULAR CONDUIT

CROSS-REFERENCE TO RELATED APPLICATIONS

This application claims the benefit of U.S. Provisional Applications Ser. Nos. 60/099,767, filed Sep. 10, 1998, and 60/104,397, filed Oct. 15, 1998.

FIELD OF THE INVENTION

The present invention relates to an apparatus for bypassing a blocked blood vessel segment, and, more particularly, to a conduit or stent positioned between the coronary artery or other blocked vessel and a chamber of the heart, such as the left ventricle of the heart, to bypass a blocked segment of the coronary artery or other blood vessel.

BACKGROUND OF THE INVENTION

Coronary artery disease is a major problem in the U.S. and throughout the world. Coronary arteries as well as other blood vessels frequently become clogged with plaque, which at the very least impairs the efficiency of the heart's pumping action, and can lead to heart attack and death. In some cases, these arteries can be unblocked through non-invasive techniques such as balloon angioplasty. In more difficult cases, a bypass of the blocked vessel is necessary.

In a bypass operation, one or more venous segments are inserted between the aorta and the coronary artery. The inserted venous segments or transplants act as a bypass of the blocked portion of the coronary artery and thus provide for a free or unobstructed flow of blood to the heart. More than 500,000 bypass procedures are performed in the U.S. every year.

Such coronary artery bypass surgery, however, is a very intrusive procedure that is expensive, time-consuming and traumatic to the patient. The operation requires an incision through the patient's sternum (sternotomy), and that the patient be placed on a bypass pump so that the heart can be operated on while not beating. A vein graft is harvested from the patient's leg, another highly invasive procedure, and a delicate surgical procedure is required to piece the bypass graft to the coronary artery (anastomosis). Hospital stays subsequent to the surgery and convalescence are prolonged.

As mentioned above, another conventional treatment is percutaneous transluminal coronary angioplasty (PTCA) or other types of angioplasty. However, such vascular treatments are not always indicated due to the type or location of the blockage, or due to the risk of emboli.

Thus, there is a need for an improved bypass system which is less traumatic to the patient.

SUMMARY OF THE INVENTION

The preferred embodiments of the present invention address the need in the previous technology by providing a bypass system that avoids the sternotomy and other intrusive procedures normally associated with coronary bypass surgery. These embodiments also free the surgeon from the multiple anastomoses necessary in the current process.

The preferred device provides a shunt for diverting blood directly from a chamber in the heart, such as the left ventricle, to the coronary artery, distal to the blockage, therefore bypassing the blocked portion of the vessel. The shunt comprises a stent or conduit adapted to be positioned in the heart wall or myocardium between the left ventricle and the coronary artery that allows for the direct passage of blood therethrough. As used herein, the terms "stent" and "conduit" are interchangeable, and refer to a device that allows for the passage of blood therethrough. The terms "myocardium" and "heart wall" are also used interchangeably. In addition, although the left ventricle is referred to throughout the description, it should be understood that the conduit described herein can be used to provide a passageway for the flow of blood from any heart chamber, not only the left ventricle.

The stent device is delivered either externally or internally through the coronary artery to a position distal to the blockage. At that position, the coronary artery, the myocardium and the wall of the left ventricle are pierced to provide a channel completely through from the coronary artery to the left ventricle of the heart. The stent is then positioned in the channel to provide a permanent passage for blood to flow between the left ventricle of the heart and the coronary artery, distal to the blockage. The stent is sized so that one open end is positioned within the coronary artery, while the other open end is positioned in the left ventricle. The hollow lumen of the stent provides a passage for the flow of blood.

The stent can be self-expandable or expanded by means of a balloon or similar device, and can be provided with various means to anchor it in position within the myocardium, such as expandable legs, hooks, barbs, collars, suture holes and the like. The stent can be formed from a plurality of rings, which can be connected to provide stability. The stent can include a valve in its interior, and can also be used to deliver drugs or other pharmaceutical compounds directly into the myocardium and the coronary circulation.

BRIEF DESCRIPTION OF THE DRAWINGS

FIG. 22 is a perspective view of a ring of a bulkhead stent in a loaded configuration FIG. 23 is a perspective view of a ring of a bulkhead stent in an inserted configuration.

FIG. 24 is a perspective view of a bulkhead stent within a delivery catheter, showing the rings of the bulkhead stent being inserted.

DETAILED DESCRIPTION OF THE PREFERRED EMBODIMENT

Figure 1A:
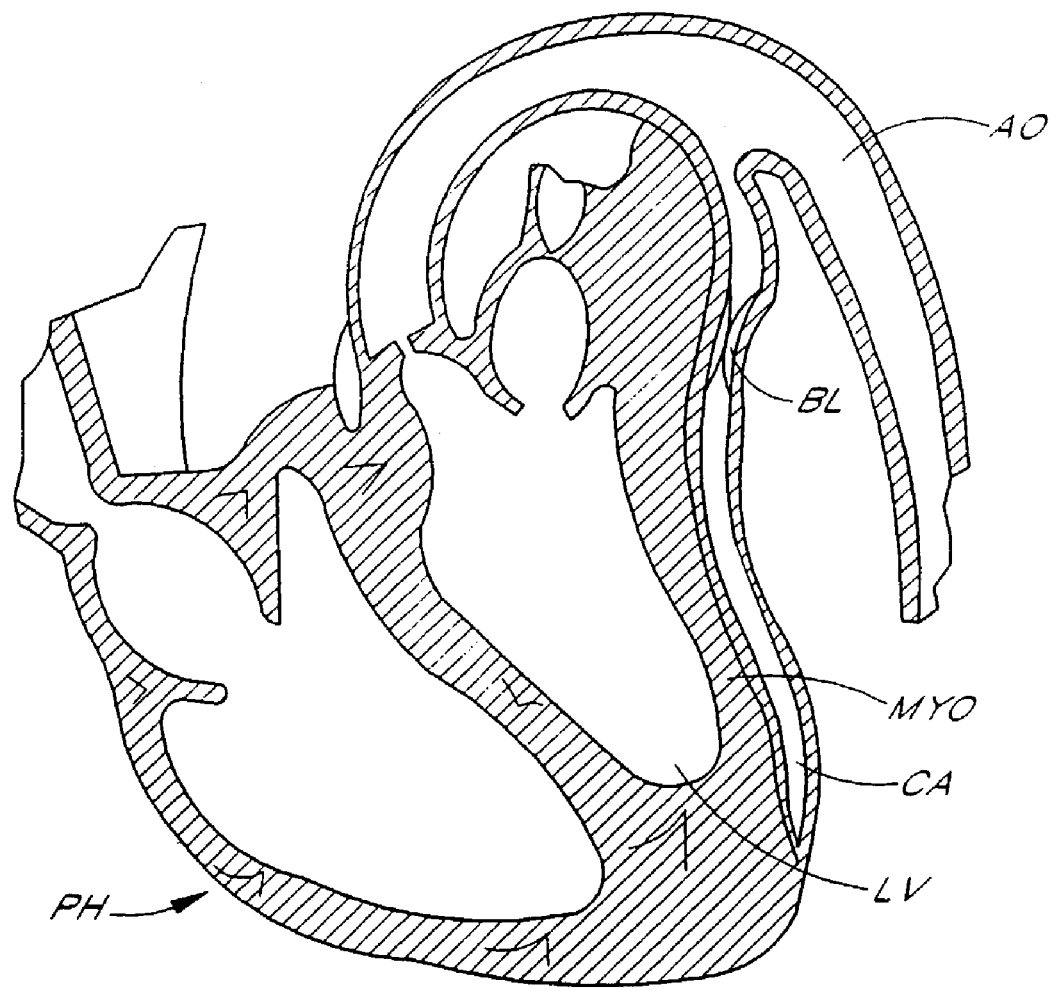
FIG. 1A is a cross-sectional view of a human heart, aorta and coronary artery.

As is well known, the coronary artery branches off the aorta and is positioned along the external surface of the heart wall. The anatomy of the human heart is illustrated in FIG. 1A. Oxygenated blood flows from the heart PH to the aorta AO, on to the rest of the body, some of the blood flowing into the coronary artery CA. In some individuals, plaque builds up within the coronary artery CA, blocking the free flow of blood and causing complications ranging from mild angina to heart attack and death.

In order to restore the flow of oxygenated blood through the coronary artery, one embodiment of the present invention provides for the shunting of blood directly from the heart to a site in the coronary artery that is distal to the blockage. A channel is formed through the wall of the coronary artery and the myocardium and into the left ventricle of the heart that lies beneath the coronary artery. A stent or conduit is positioned in the passage to keep it open, and allow for the flow of oxygenated blood directly from the heart into the coronary artery. Again, it should be understood that while the insertion of the conduit in the myocardium between the left ventricle and the coronary artery is described in detail below, this is merely exemplary and use of the conduit between other chambers of the heart and the coronary artery, and between blood vessels is also contemplated.

The principles of the present invention are not limited to left ventricular conduits, and include conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. For example, in one preferred embodiment of the present invention, the conduit communicates from the left ventricle, through the myocardium, into the pericardial space, and then into the coronary artery. However, other preferred embodiments are disclosed, including direct transmyocardial communication from a left ventricle, through the myocardium and into the coronary artery. Thus, as emphasized above, the term "transmyocardial" should not be narrowly construed in connection with the preferred fluid communication conduits, and other non-myocardial and even non-cardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the occlusions which are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Moreover, the conduits are not necessarily stented or lined with a device but can comprise mere tunnels or openings formed in the tissues of the patient.

The conduits of the present invention preferably comprise both integral or one-piece conduits as well as plural sections joined together to form a continuous conduit. The present conduits can be deployed in a variety of methods consistent with sound medical practice including vascular or surgical deliveries, including minimally invasive techniques. For example, various preferred embodiments of delivery rods and associated methods may be used. In one embodiment, the delivery rod is solid and trocar-like. It may be rigid or semi-rigid and capable of penetrating the tissues of the patient and thereby form the conduit, in whole or in part, for purposes of fluid communication. In other preferred embodiments, the delivery rods may be hollow so as to form the conduits themselves (e.g., the conduits are preferably self-implanting or self-inserting) or have a conduit mounted thereon (e.g., the delivery rod is preferably withdrawn leaving the conduit installed). Thus, the preferred conduit device and method for installation is preferably determined by appropriate patient indications in accordance with sound medical practices.

In some individuals, aortic insufficiency or peripheral venous insufficiency occurs. Aortic insufficiency is the leakage of blood through the aortic valve, resulting in a backflow of blood into the left ventricle. The heart compensates for the backflow of blood by pumping harder, resulting in hypertrophy (thickening of the heart muscle) and dilation of the left ventricle wall. Left untreated, heart failure can result. In venous insufficiency, the heart valves are unable to prevent the backflow of blood. This too can result in heart failure. Accordingly, one embodiment of the invention provides for the use of a conduit placed within the heart wall to improve the flow of oxygenated blood through the body.

Figure 1B:
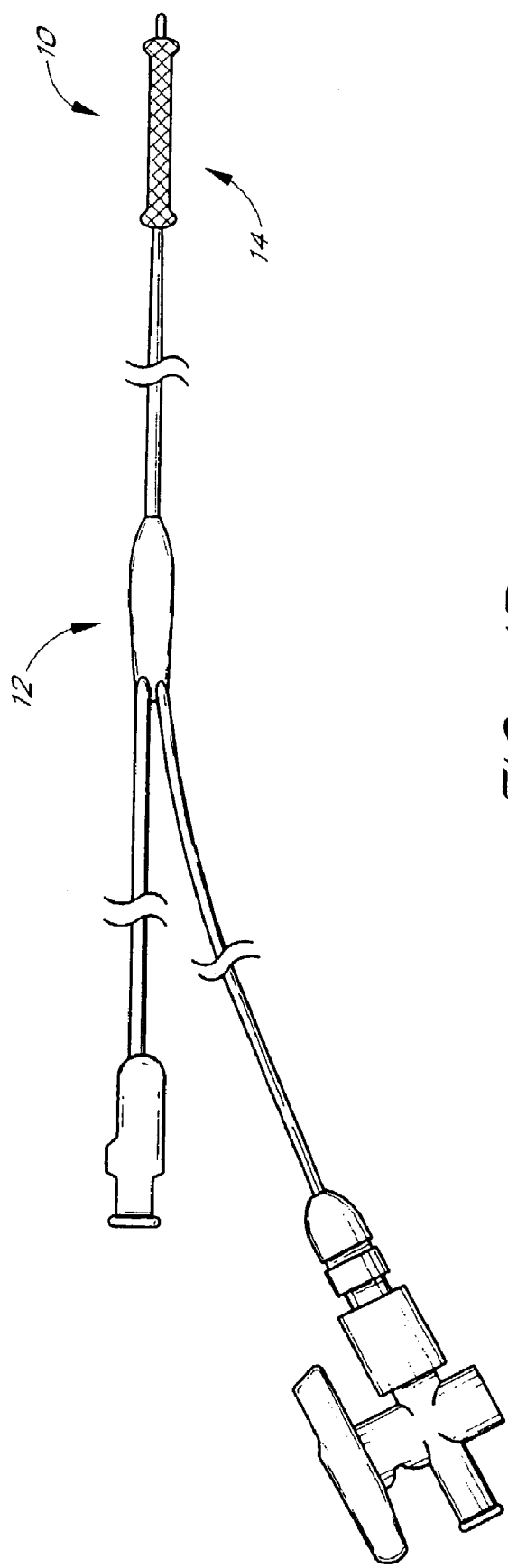
FIG. 1B is a side view of one embodiment of an expandable stent and the balloon catheter used for stent delivery.
Figure 2:
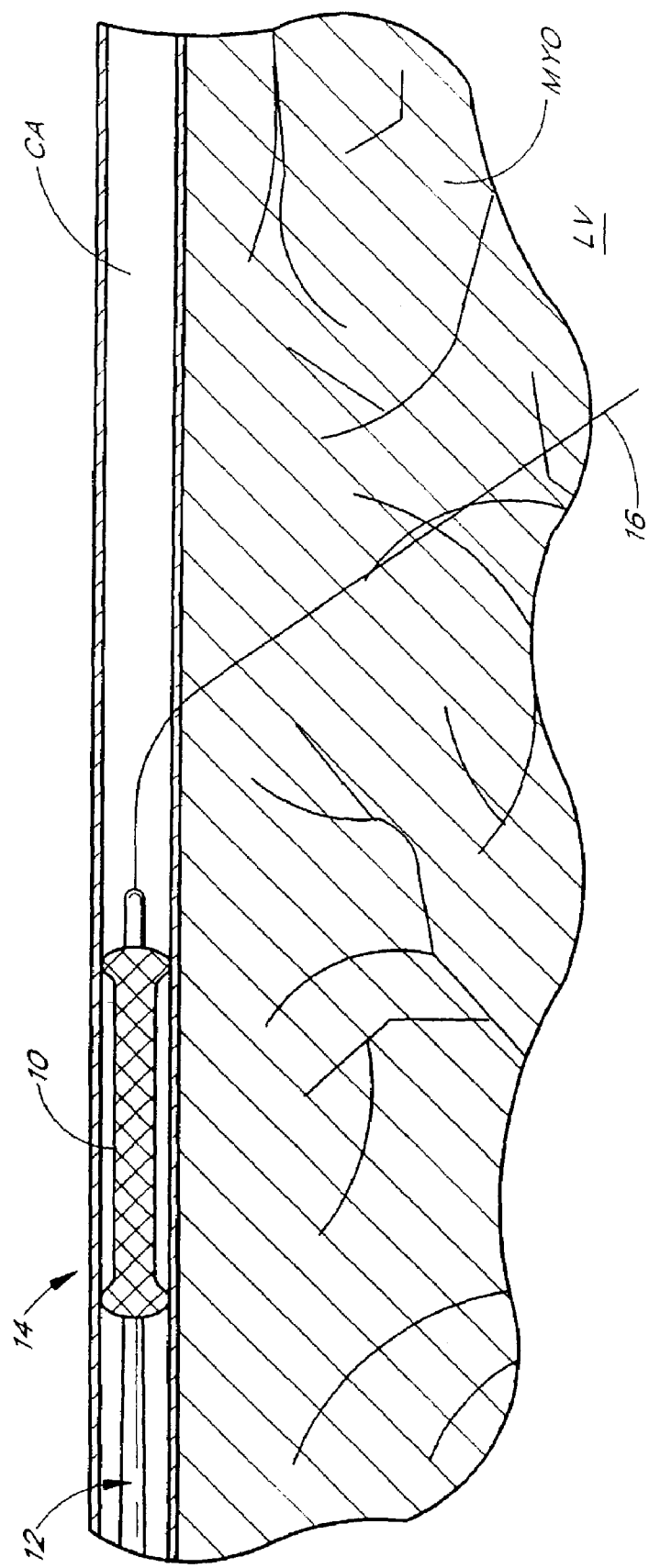
FIG. 2 is a side view of the stent of FIG. 1B mounted on the distal end of the catheter for delivery into the myocardium, with the coronary artery and myocardium shown cut-away.

A first embodiment of the present invention is illustrated in FIG. 1B. This embodiment is a balloon-expanded stent 10. The stent 10 is introduced as described below, using a high-pressure balloon catheter 12 to deploy the stent 10 once it is properly positioned in the myocardium MYO (FIG. 2). When the stent 10 is positioned inside the myocardial wall MYO, the balloon 14 is inflated to expand the stent 10 and open the conduit from the left ventricle LV into the coronary artery CA. The stent 10 can include attachment mechanisms not limited to hooks, barbs, flanges, large collars, suture holes and/or other means to ensure a seal is created between the coronary artery CA and the wall of the myocardium MYO and to prevent the threat of stent 10 migration. When the attachment of the stent 10 is completed, the remaining catheter assembly 12 is removed, leaving the stent 10 in place. Upon deflating the balloon 14, the stent 10 will remain open. Because of the shape of this stent 10, a dumbbell shaped balloon 14 is preferably used to ensure proper expansion, as described below.

FIGS. 1B through 4 illustrate the introduction of the balloon-expanded stent 10 into the myocardial wall MYO. FIG. 1B illustrates the stent 10 mounted over the balloon 14 on the distal end of the stent introducer catheter 12. FIG. 2 illustrates the stent introducer catheter 12 following the path created by a puncture wire 16 extending past the distal end of the introducer catheter 12, and used to access the left ventricle LV through the coronary artery CA and myocardium MYO. Further details regarding conduits and conduit delivery systems are described in copending patent applications entitled DELIVERY METHODS FOR LEFT VENTRICULAR CONDUIT, U.S. patent application Ser. No. 09/368,868, LEFT VENTRICULAR CONDUIT WITH BLOOD VESSEL GRAFT, U.S. patent application Ser. No. 09/369,061 VALVE DESIGNS FOR LEFT VENTRICULAR CONDUIT, U.S. patent application Ser. No. 09/368,393, LEFT VENTRICULAR CONDUITS TO CORONARY ARTERIES AND METHODS FOR CORONARY BYPASS, U.S. patent application Ser. No. 09/369,039, and BLOOD FLOW CONDUIT DELIVERY SYSTEM AND METHOD OF USE, U.S. patent application Ser. No. 09/368,644, all filed on Aug. 4, 1999, and U.S. Pat. Nos. 5,429,144 and 5,662,124, the disclosures of which are all hereby incorporated by reference in their entirety.

Figure 3:
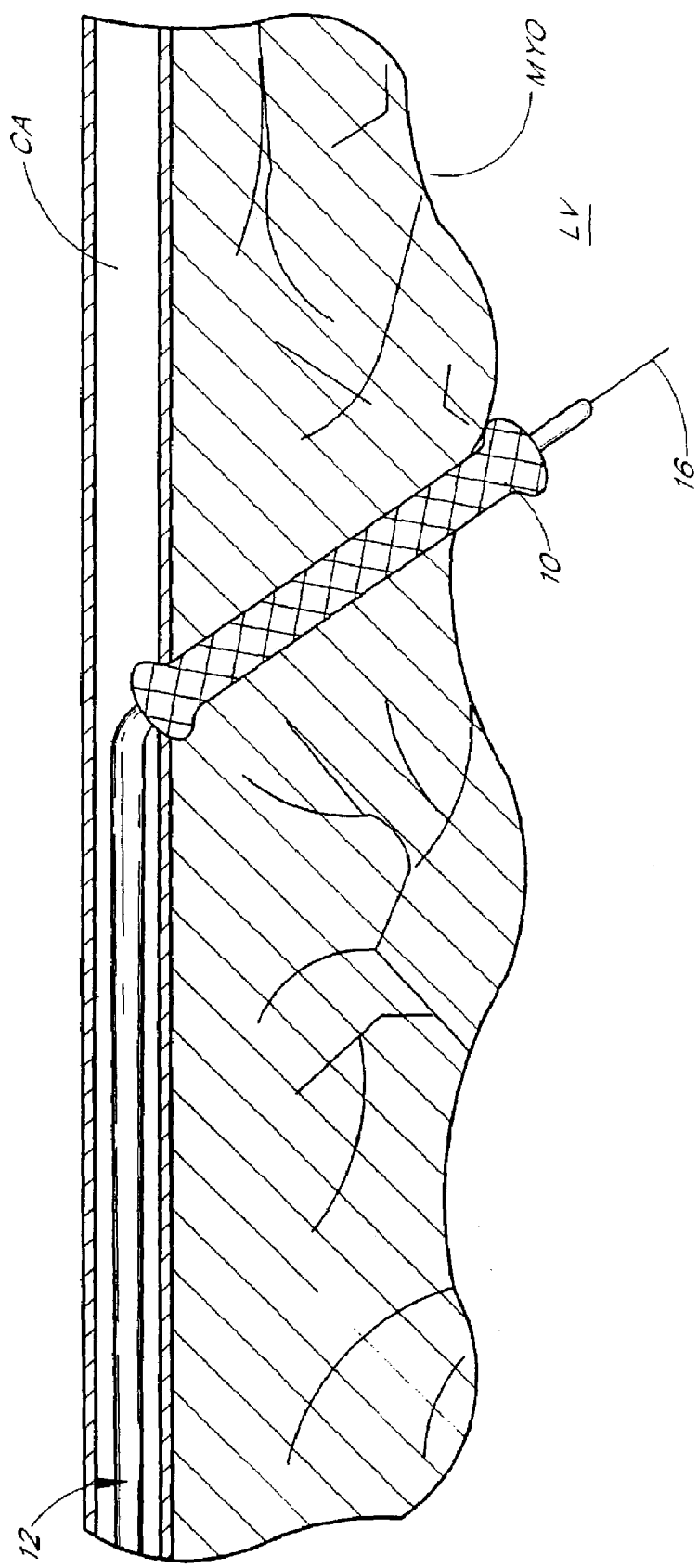
FIG. 3 is a side view of the distal end of the stent/catheter assembly of FIG. 1B positioned in the myocardium, with the coronary artery and myocardium shown cut-away.
Figure 4:
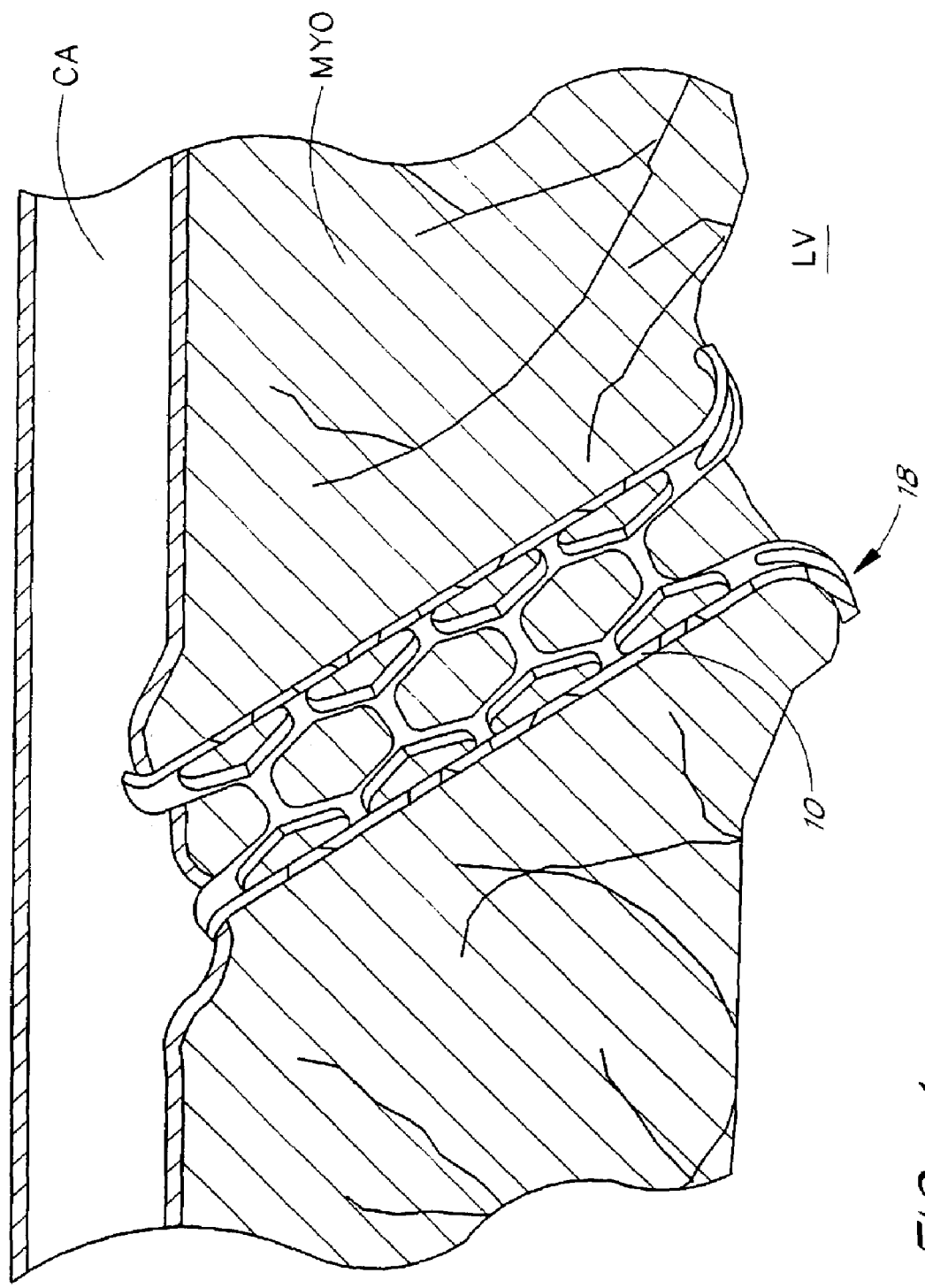
FIG. 4 is a cross-sectional side view of the stent of FIG. 1B positioned within the myocardium after removal of the catheter used for delivery.

FIG. 3 illustrates the non-expanded stent 10 positioned inside the myocardial wall MYO prior to inflation of the balloon 14. FIG. 4 illustrates an expanded stent 10 in position, with the introducer catheter 12 removed. Because of the way the attachment mechanisms 18 expand on this stent 10, a dumbbell shaped balloon 14 is preferably used to flare out the ends of the stent 10. These flared edges 18 maintain the stent 10 in its proper position in the heart wall MYO and provide a seal between the coronary artery CA and the outer heart wall MYO.

The second embodiment of the stent or conduit incorporates a self-expanding stent 20, illustrated in FIGS. 5–8. The stent 20, having a retaining sheath 26 to hold it in a non-expanded configuration, is introduced into the wall of the myocardium MYO as follows. The stent delivery catheter 22 is advanced over a puncture mechanism 24 and into the wall of the myocardium MYO as described above. When the stent 20 is properly seated in the myocardial wall MYO, its retaining sheath 26 is withdrawn, allowing the stent 20 to expand and open a conduit from the ventricle LV to the coronary artery CA. This stent 20 also includes attachment mechanisms not limited to hooks, barbs, flanges, large collars, suture holes and/or other means to ensure a seal is created between the artery CA and the wall of the myocardium MYO, and to prevent the threat of stent 20 migration. When the positioning is completed, the remaining catheter assembly 22 is removed, leaving the stent 20 in place.

Figure 5:
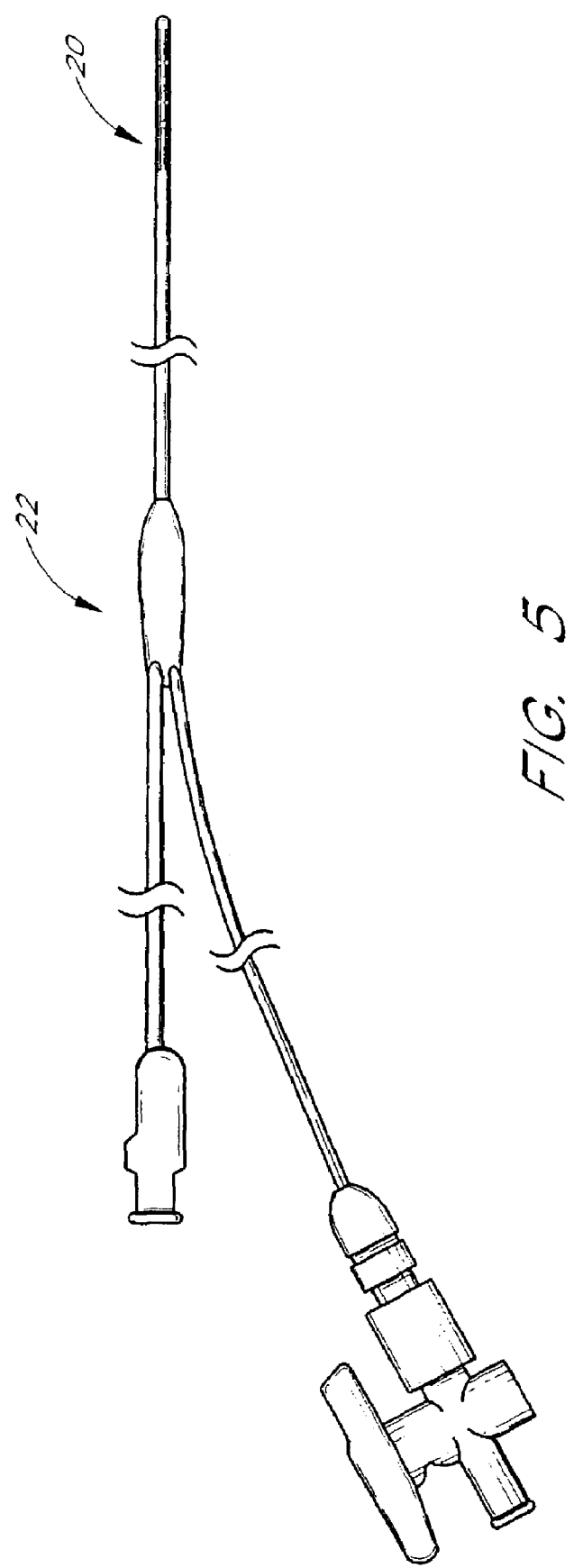
FIG. 5 is a side view of another embodiment of the stent and the catheter used for stent delivery.
Figure 6:
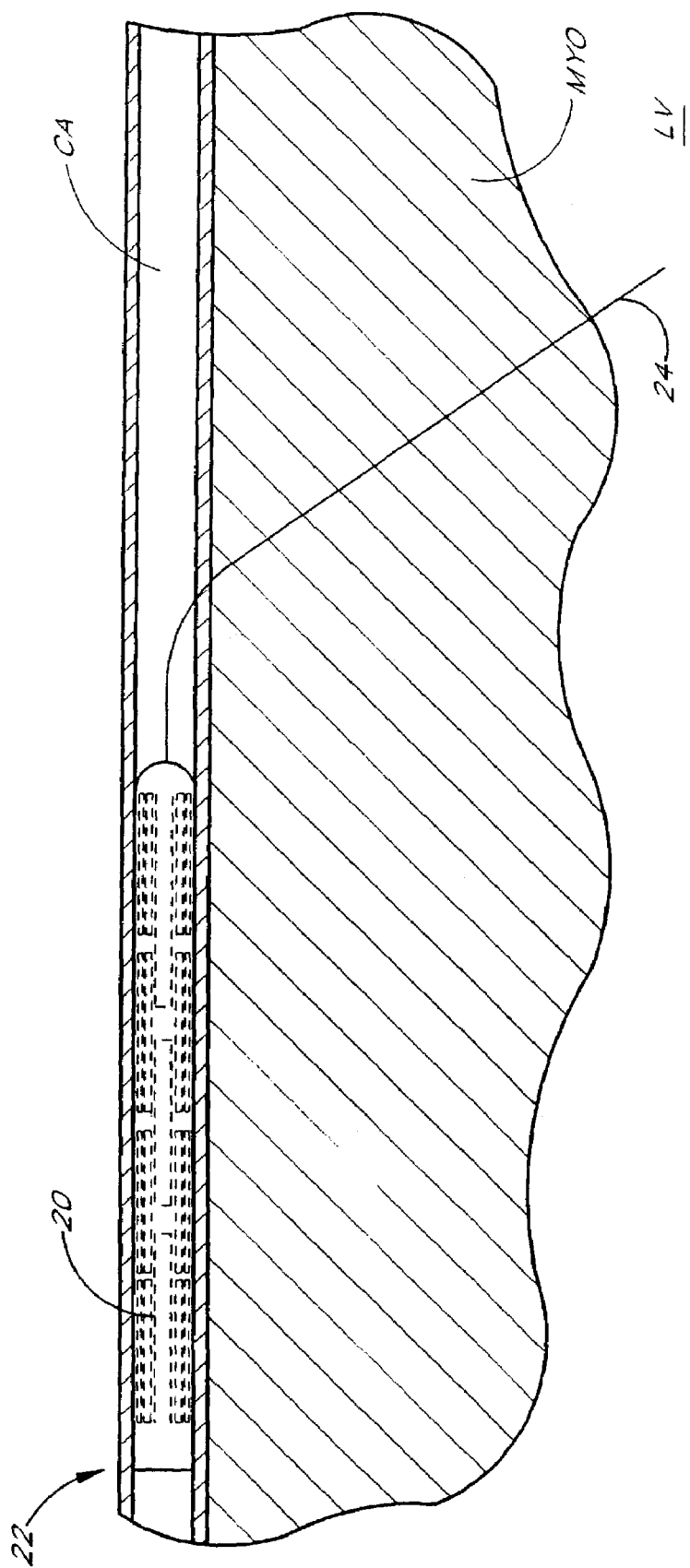
FIG. 6 is a cross-sectional side view of the catheter and puncture device used to introduce the self-expanding stent of FIG. 5 into the myocardium.
Figure 7:
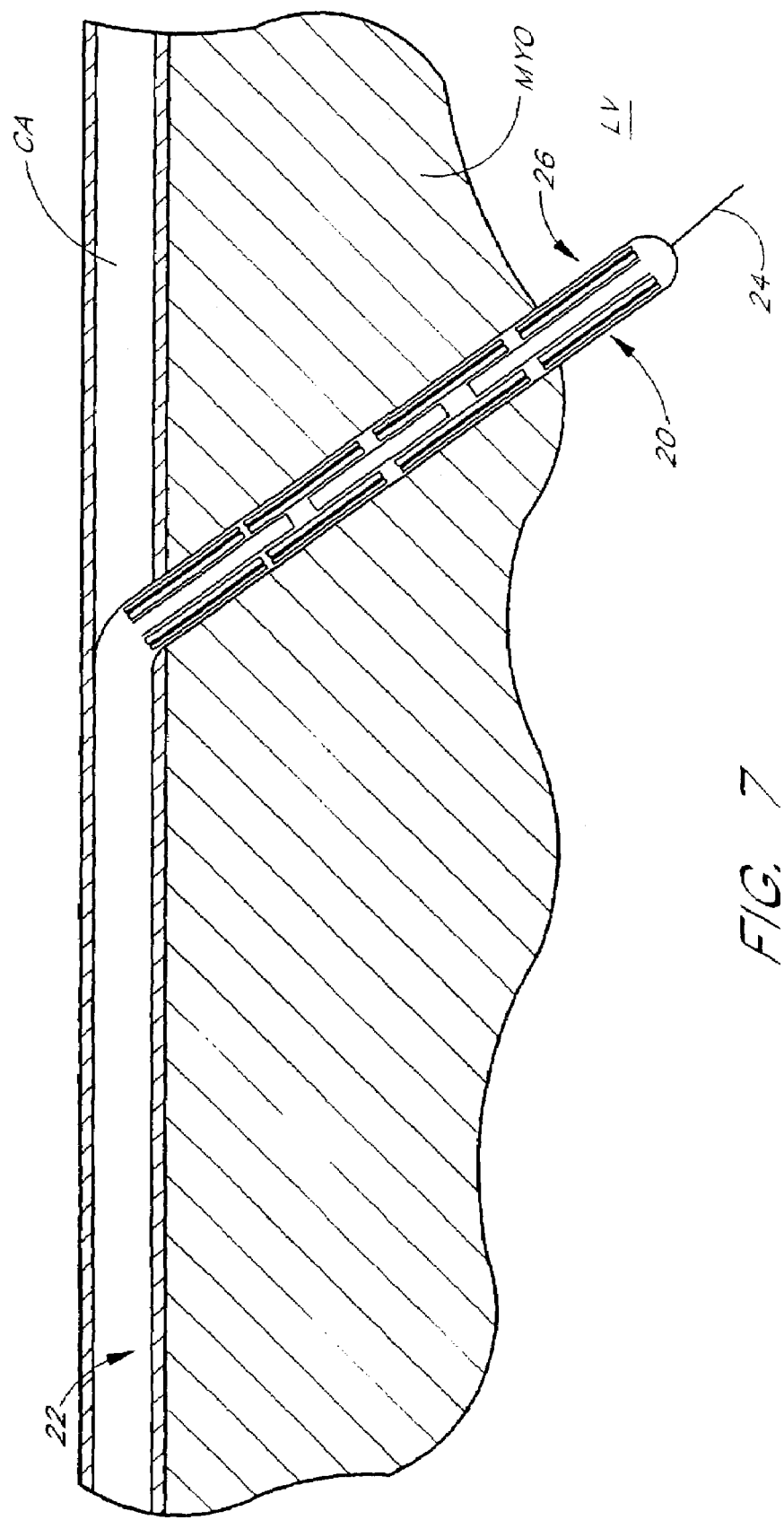
FIG. 7 is a cross-sectional side view of the stent/catheter assembly of FIG. 5 positioned in the myocardium.
Figure 8:
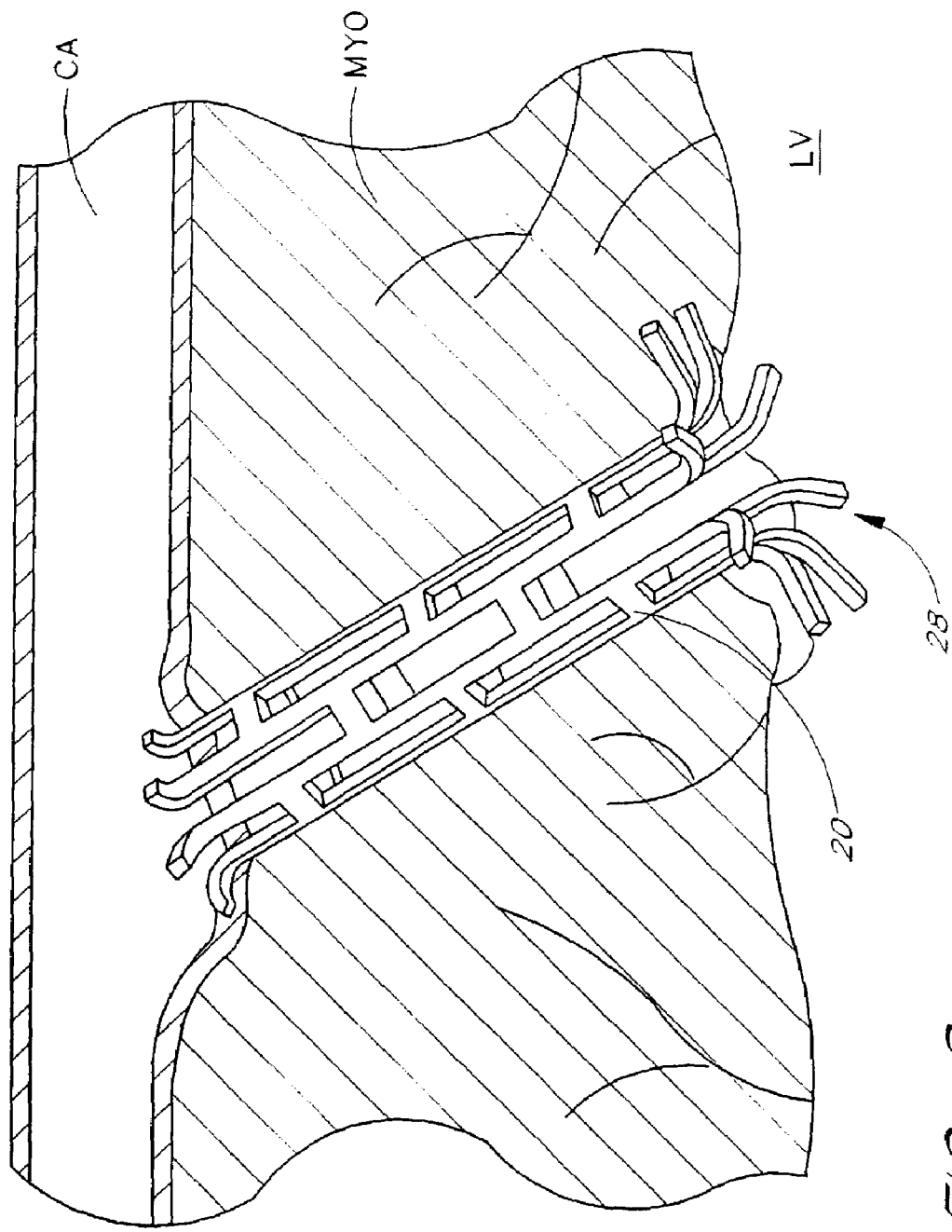
FIG. 8 is a side view of the self-expanding stent of FIG. 5 positioned within the myocardium after removal of the catheter and puncture device, with the coronary artery and myocardium shown cut-away.

The self-expanding stent 20 mounted on the distal end of the stent introducer catheter 22 is illustrated in FIG. 5. FIG. 6 illustrates the stent introducer 22 following the path created by a puncture wire 24 used to form the passage between the coronary artery CA and the left ventricle LV. FIG. 7 illustrates a non-expanded stent 20 located in position on the stent introducer catheter 22 with the introducer catheter 22 in position in the heart wall MYO. FIG. 8 illustrates the self-expanding stent 20 in position, with the introducing catheter 22 removed. Flared edges 28 on the stent 20 maintain its proper position in the heart wall MYO and provide a seal between the coronary vessel CA and outer surface of the heart MYO.

For the stent designs described above, additional anchoring methods may be desired to maintain the stent's proper position and/or create a leak-free seal in the coronary artery. Suitable attachment mechanisms include a set of barbs located on the stent body or flares and a collar on the coronary side to help seal and prevent blood from exiting the gap between the vessel and outer heart wall. The stent can also be anchored in place by applying sutures. The stent can include holes at either end to facilitate the placement of these anchoring sutures. A suture gun can be used to apply multiple sutures at the same time. In addition, the stents can be lined, if desired, with materials such as polymers, for example polytetrafluoroethylene (PTFE), silicone or GOR-TEX, to provide for the ease of blood flow therethrough.

Figure 9:
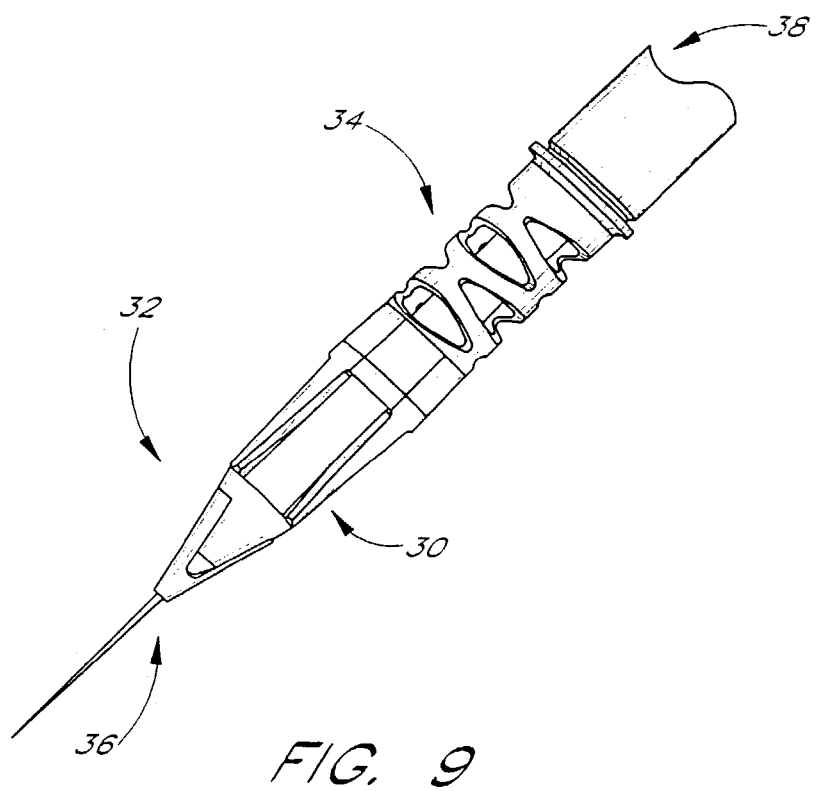
FIG. 9 is a perspective view of another embodiment of the stent having expandable legs, showing the stent mounted on the distal end of the introducer catheter.
Figure 10:
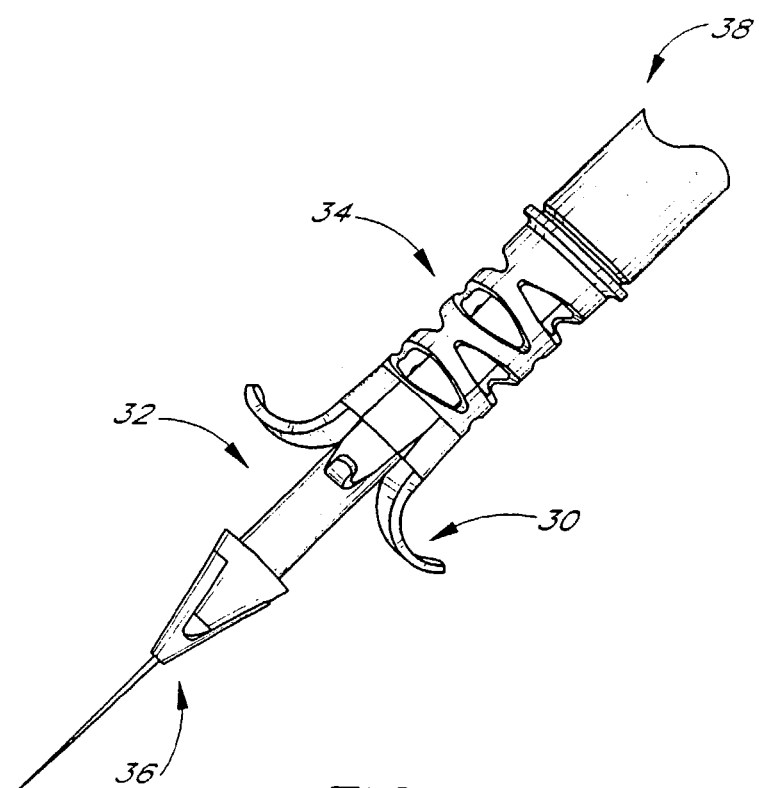
FIG. 10 is a perspective view of the stent of FIG. 9, showing the distal end of the introducer catheter pushed forward to allow the legs of the stent to expand.
Figure 11:
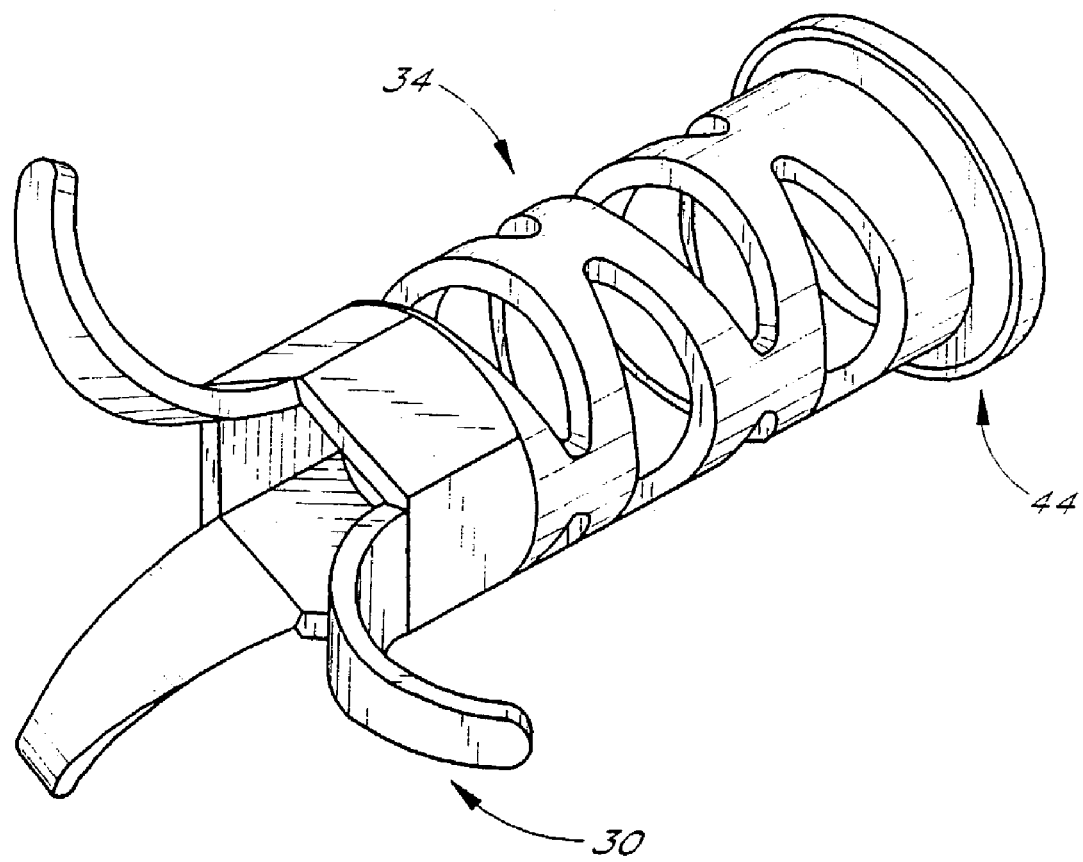
FIG. 11 is a perspective view of the stent of FIG. 9, showing the legs of the stent in an expanded position.

A third embodiment of the stent design, illustrated in FIGS. 9–11, incorporates attachment flanges or "legs" 30 that expand after introduction into the myocardium to hold the stent 34 in place. The puncture instrument 32 and stent 34 are mated together and are advanced into the myocardial wall as a single unit. The puncture instrument's distal end 36 is shaped in a "nose-cone" configuration, which is responsible for containing the legs 30 of the stent 34 while it is being introduced into the wall of the myocardium. When the stent 34 is in the proper position in the myocardial wall, the nose cone 36 is pushed forward, releasing the attachment legs 30 of the stent 34. The internal diameter (ID) of the stent 34 is large enough to allow the nose cone 36 to pass back through. The stent 34 is then released from the catheter 38 and the catheter 38 is removed.

FIG. 9 illustrates the stent 34 mounted on the introducer catheter 38. The expanding legs 30 of the stent 34 are held in place by the nose cone 36 on the distal end of the catheter 38 that acts as a dilator. The catheter assembly 38 is advanced over a puncture wire if desired, into proper position in the myocardium, and the nose cone 36 is pushed forward allowing the legs 30 to expand as shown in FIG. 10. The nosecone/puncture assembly 32, 36 is then withdrawn through the lumen of the stent 34. When the nose-cone/puncture assembly 32, 36 is removed, the stent 34 can be pushed off the introducer catheter 38 and remains in the myocardium in the position shown in FIG. 11. FIG. 11 also illustrates a sealing collar 44 that may be used in the interface between the coronary artery and the outer wall of the heart to prevent hemorrhaging around the stent 34 and to hold the stent 34 in place. Sutures can be used to ensure that the stent is maintained in its proper position and prevent migration.

Figure 12:
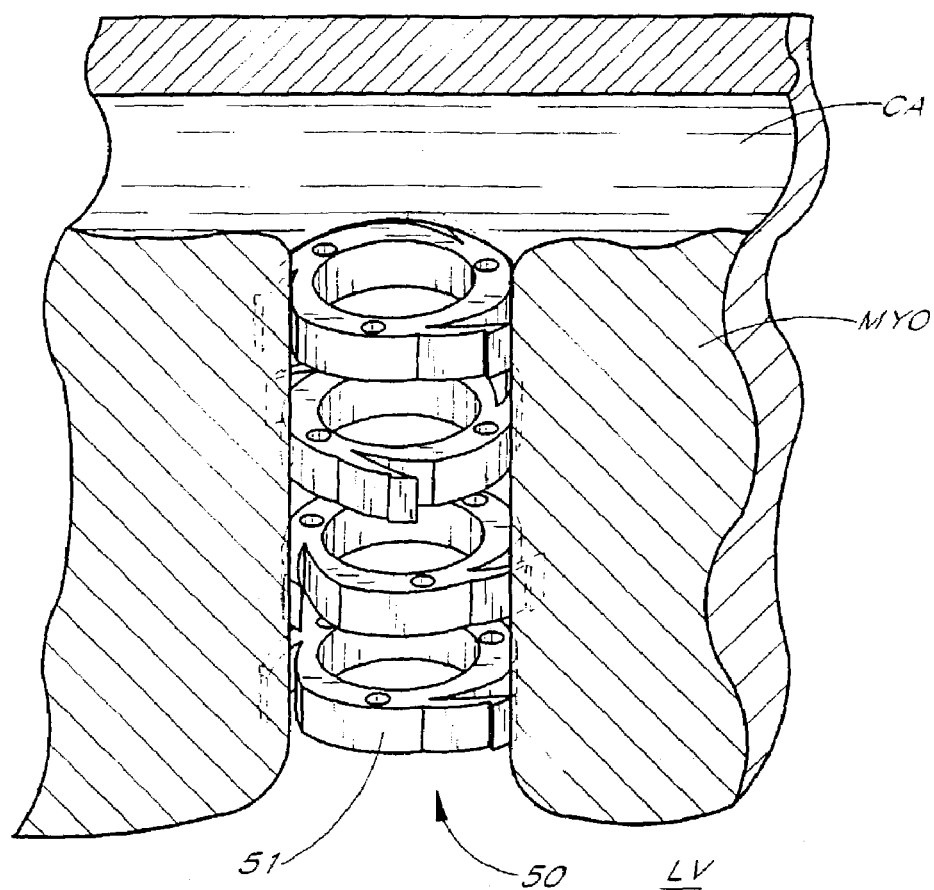
FIG. 12 is a side view of another embodiment of the stent positioned within the myocardium, with the coronary artery and myocardium shown cut-away.

FIG. 12 illustrates a further embodiment of the present invention, a "bulkhead" stent 50. This stent 50 consists of a plurality of rings, which are placed in the myocardium MYO. The rings 50 form a passage through which blood flows from a chamber in the heart, such as the left ventricle LV, directly into the coronary artery CA. The stent 50 is preferably formed of biocompatible material such as a metal or polymer. A gun or other suitable device can be used to implant the stent 50 in the myocardium MYO.

If desired, the separate units or rings of the stent 50 can be connected via a wire, suture thread, or similar means. The wire is threaded through the holes 51 located in each ring. Connecting the rings of the stent 50 in this manner serves to make the stent 50 more stable and to prevent the migration of the individual units. If desired, a valve (not shown) can be incorporated into the stent 50 to help prevent the backflow of blood into the left ventricle LV. Additional details regarding valve designs are disclosed in the above referenced copending applications entitled LEFT VENTRICULAR CONDUIT WITH BLOOD VESSEL GRAFT, U.S. patent application Ser. No. 09/369,061, VALVE DESIGNS FOR LEFT VENTRICULAR CONDUIT, U.S. patent application Ser. No. 09/368,393and LEFT VENTRICULAR CONDUITS TO CORONARY ARTERIES AND METHODS FOR CORONARY BYPASS, U.S. patent application Ser. No. 09/369,039, filed on Aug. 4, 1999, all of which are incorporated by reference in their entirety.

Figure 13:
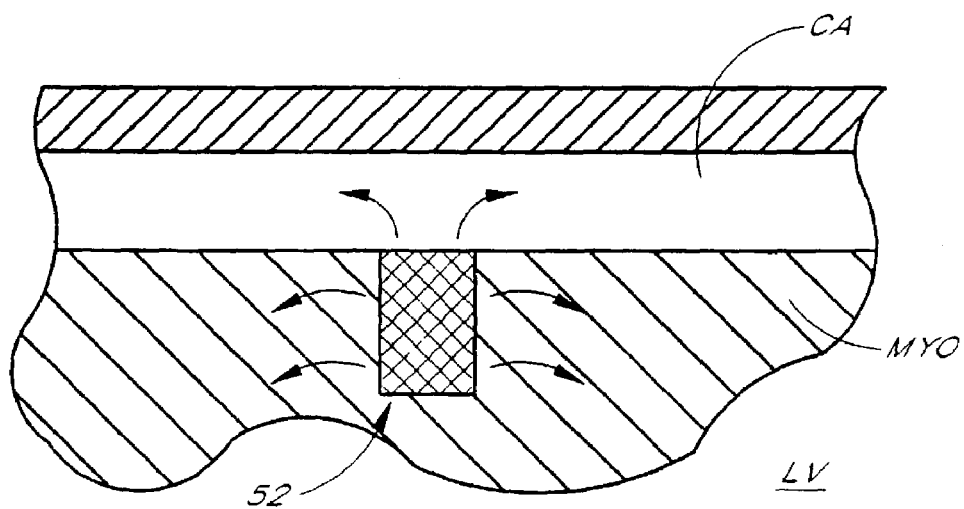
FIG. 13 is a side view of a biodegradable stent positioned within the myocardium, with the coronary artery and myocardium shown cut-away.

If desired, the stent or conduit of the present invention can be formed of biodegradable or bioabsorbable materials and/or used to deliver drugs directly into the myocardium and the coronary circulation. Such a stent 52 is illustrated in FIG. 13. The biodegradable stent 52 can extend only partially through the myocardium MYO as illustrated in FIG. 13, but can also extend entirely through from the left ventricle LV to the coronary artery CA. Once positioned in the myocardium MYO, the stent 52 degrades, dissolves or is absorbed over time to release drugs, genes, angiogenesis or growth factors, or other pharmaceutical compounds directly into the heart muscle MYO and the coronary artery CA, as shown by the arrows in FIG. 13. Bioabsorbable materials include, but are not limited to, polymers of the linear aliphatic polyester and glycolide families, such as polylactide and polyglycolide. Further details are described in the above-referenced application entitled LEFT VENTRICULAR CONDUITS TO CORONARY ARTERIES AND METHODS FOR CORONARY BYPASS U.S. patent application Ser. No. 09/369,039, filed on Aug. 4, 1999.

Figure 14:
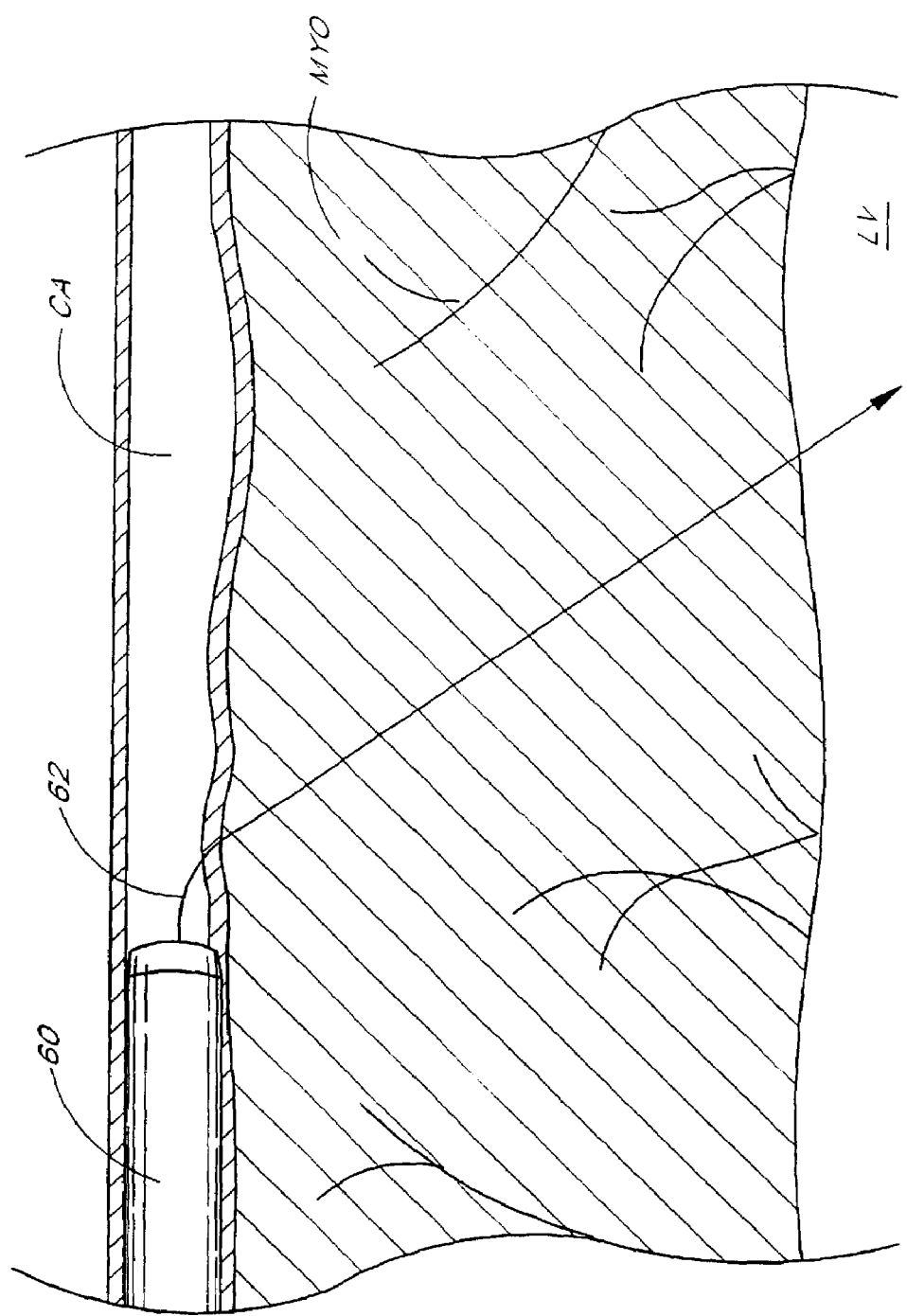
FIG. 14 is a side view of a catheter and puncture device used to introduce a bulkhead stent into the myocardium, with the coronary artery and myocardium shown cut-away.
Figure 15:
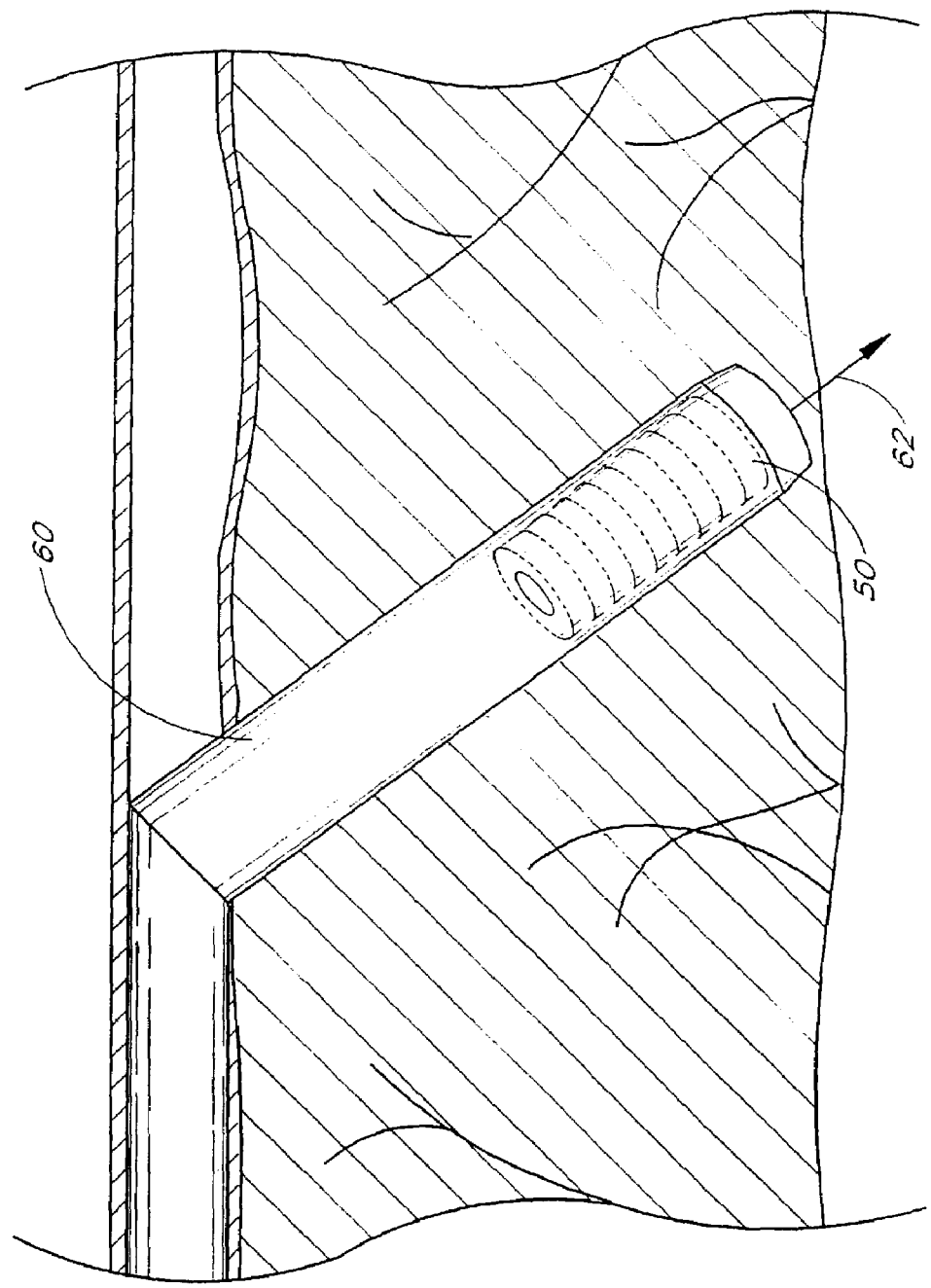
FIG. 15 is a side view of the stent/catheter assembly of FIG. 14 positioned in the myocardium, with the coronary artery and myocardium shown cutaway.
Figure 16:
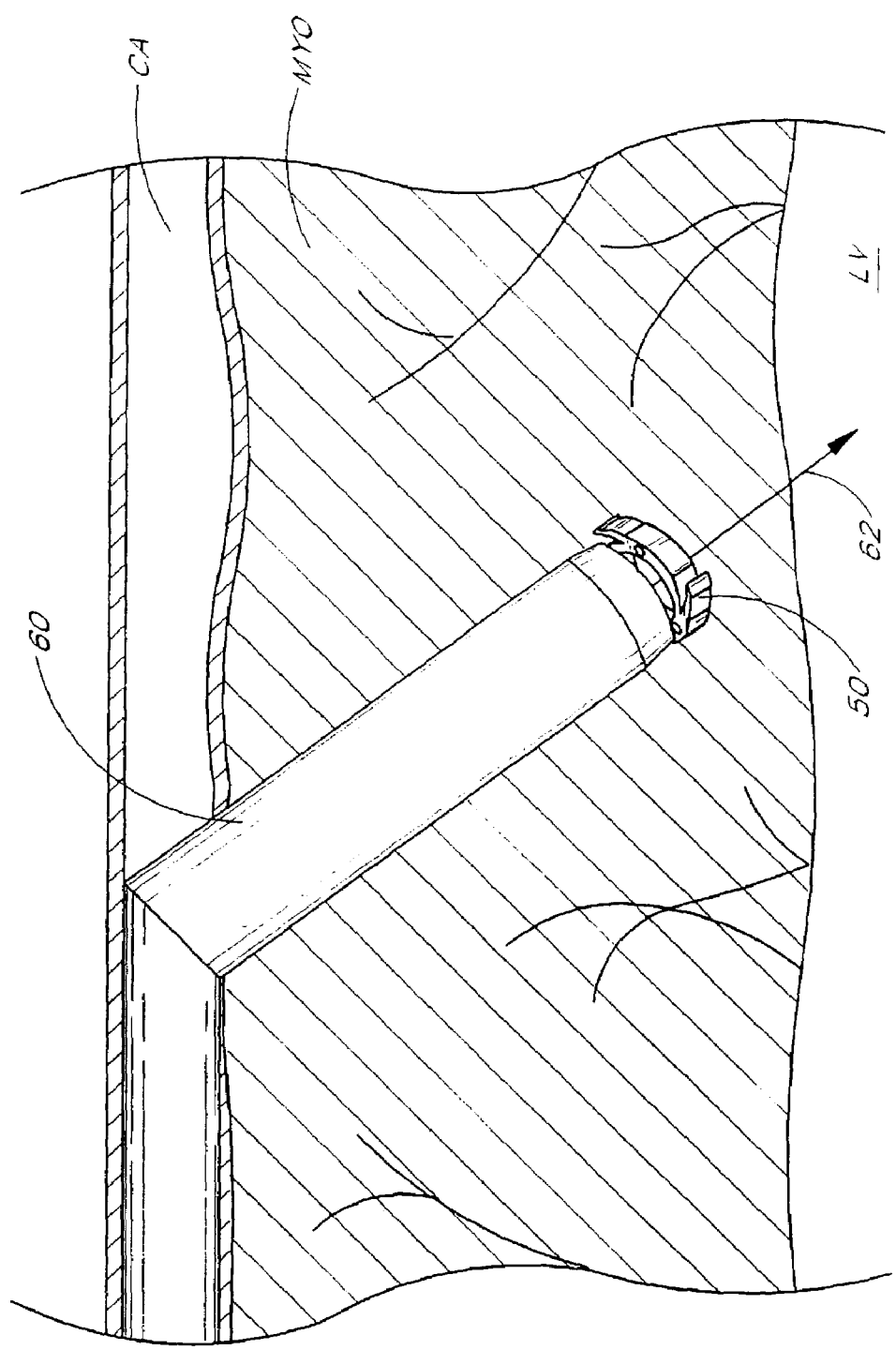
FIGS. 16–19 are progressive side views of the stent/catheter assembly of FIG. 14, showing the bulkhead stent being deployed into the myocardium.
Figure 17:
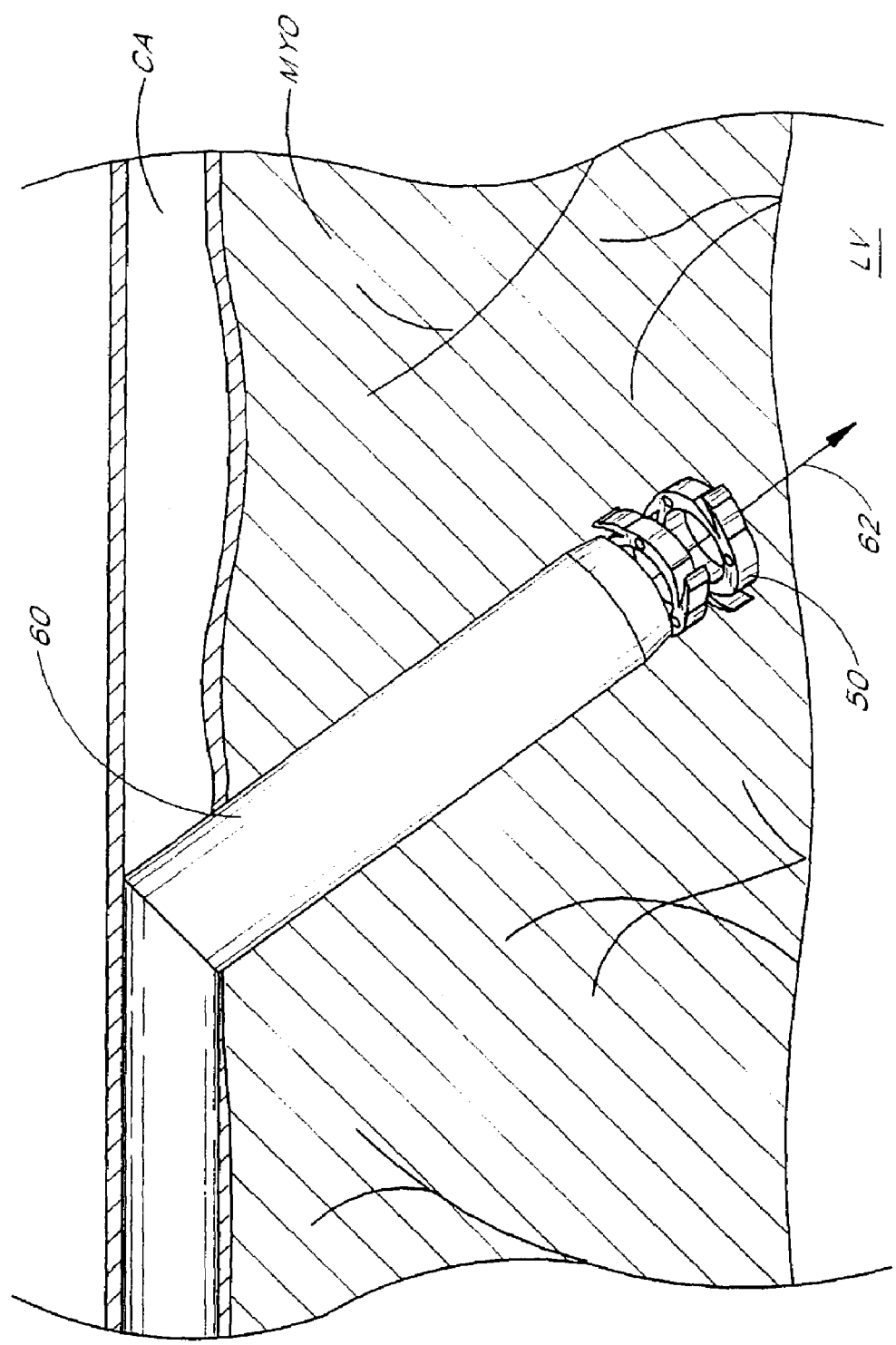

Turning now to FIGS. 14–26, there is illustrated in greater detail one preferred method and apparatus for providing a bulkhead stent 50, as shown in FIG. 12, into the myocardium MYO. As shown in FIG. 14, a stent delivery catheter 60 is advanced over a puncture wire 62 and into the wall of the myocardium MYO as described above. The stent delivery catheter 60 follows the path created by the puncture wire 62 used to form the passage between the coronary artery CA and the left ventricle LV. FIG. 15 illustrates a bulkhead stent 50 still located in position inside the stent delivery catheter 60 with the catheter 60 in position in the heart wall MYO.

Figure 18:
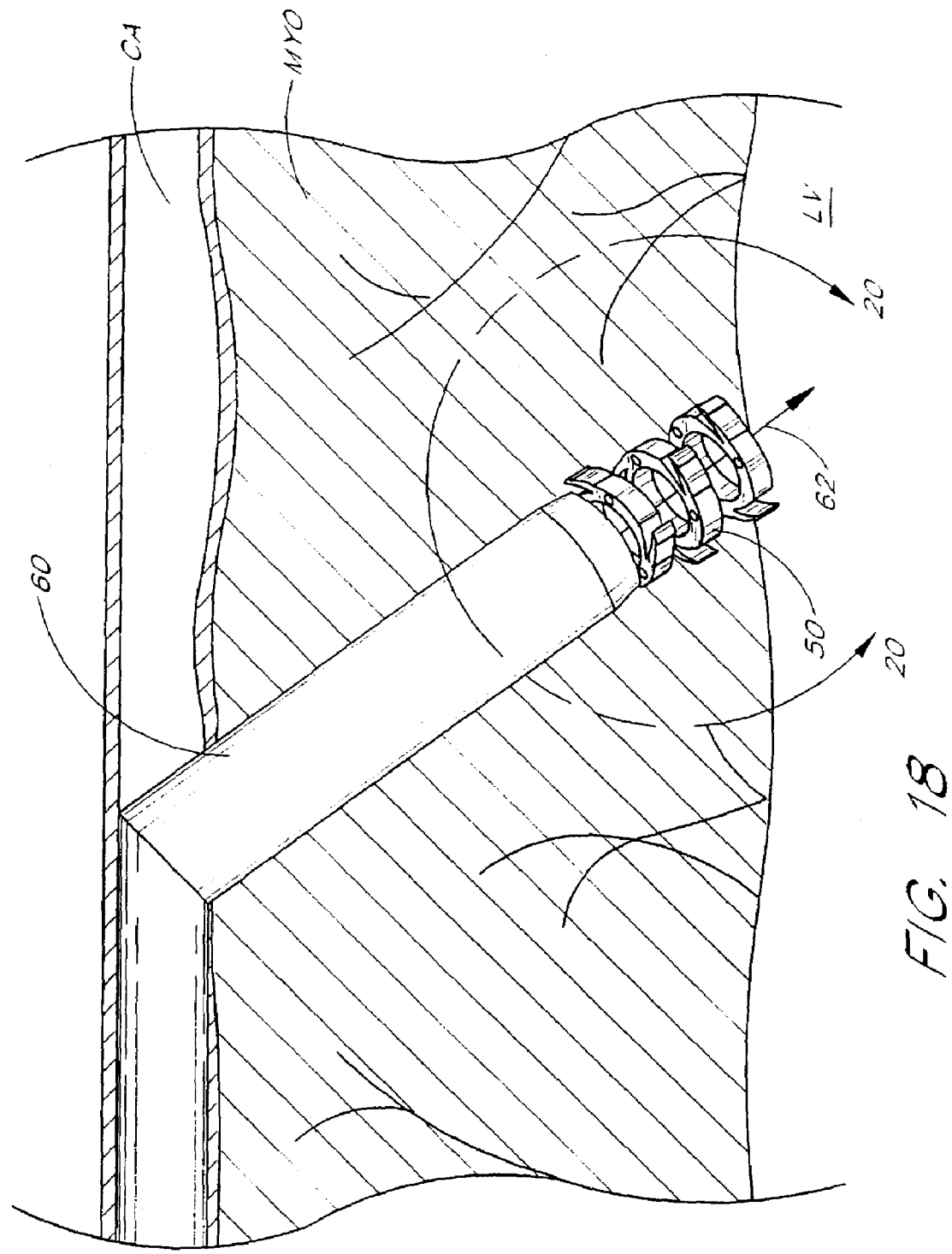
Figure 19:
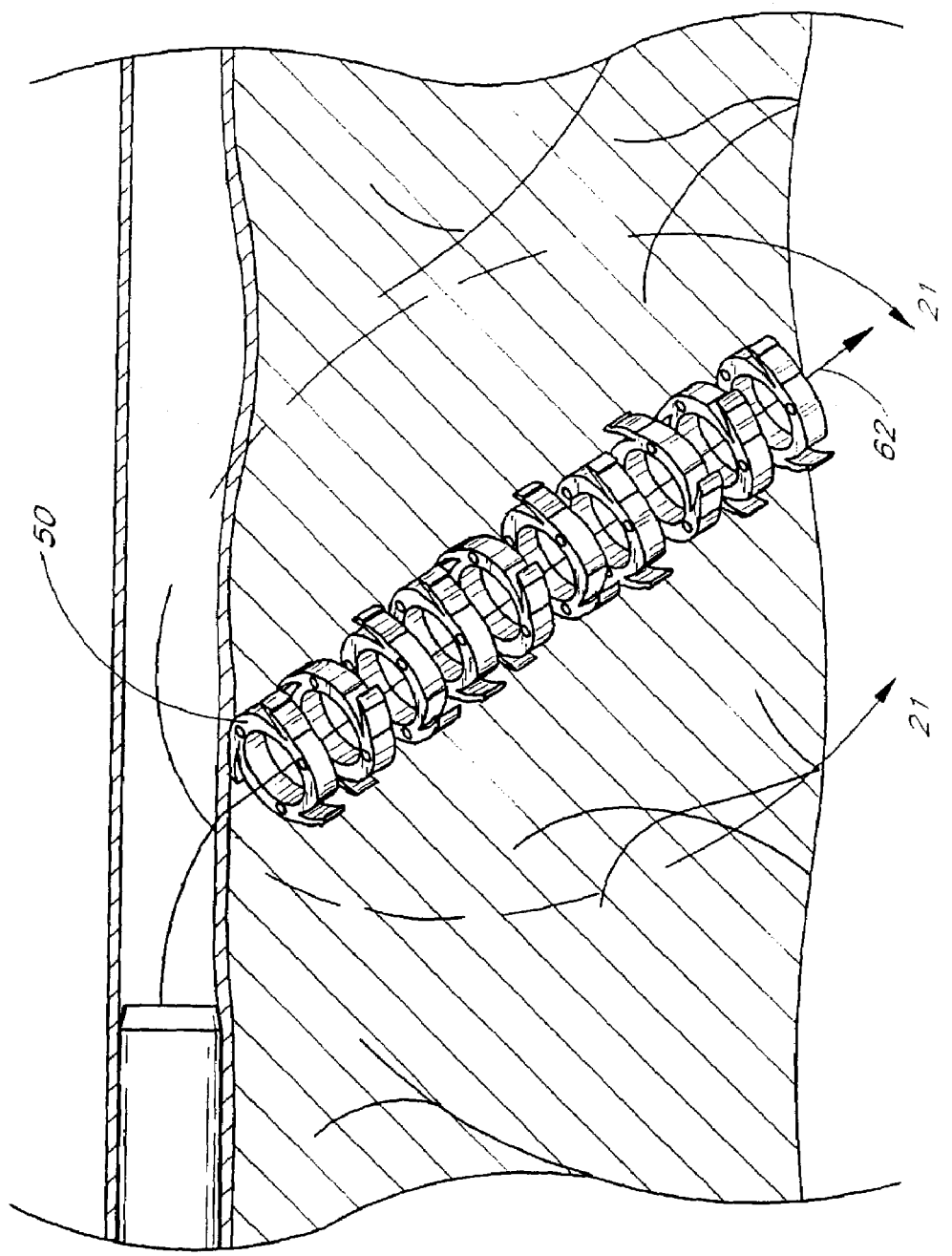
Figure 20:
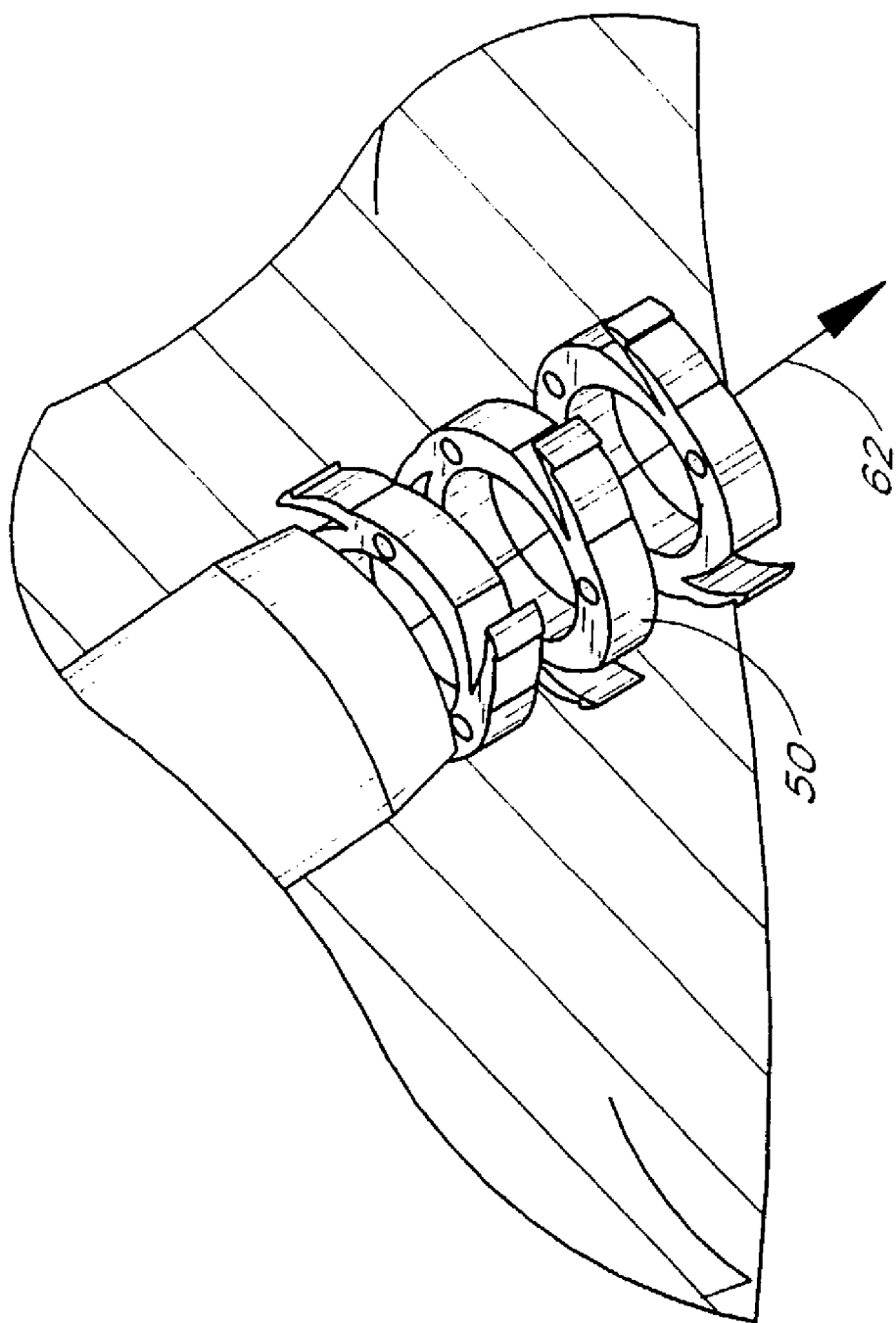
FIGS. 20 and 21 are enlarged views of FIGS. 18 and 19, respectively, showing the bulkhead stent being deployed into the myocardium.
Figure 21:
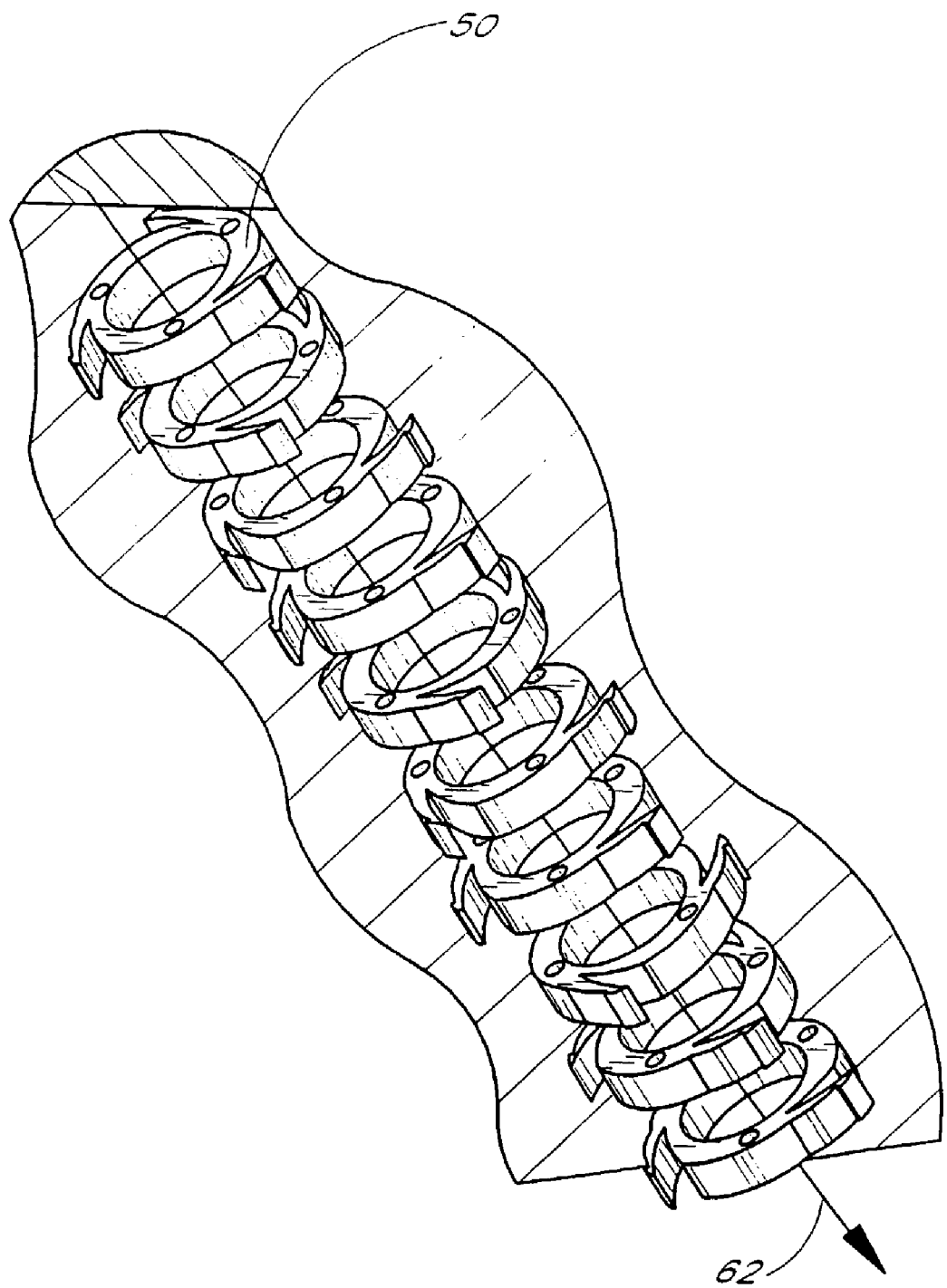
Figure 25:
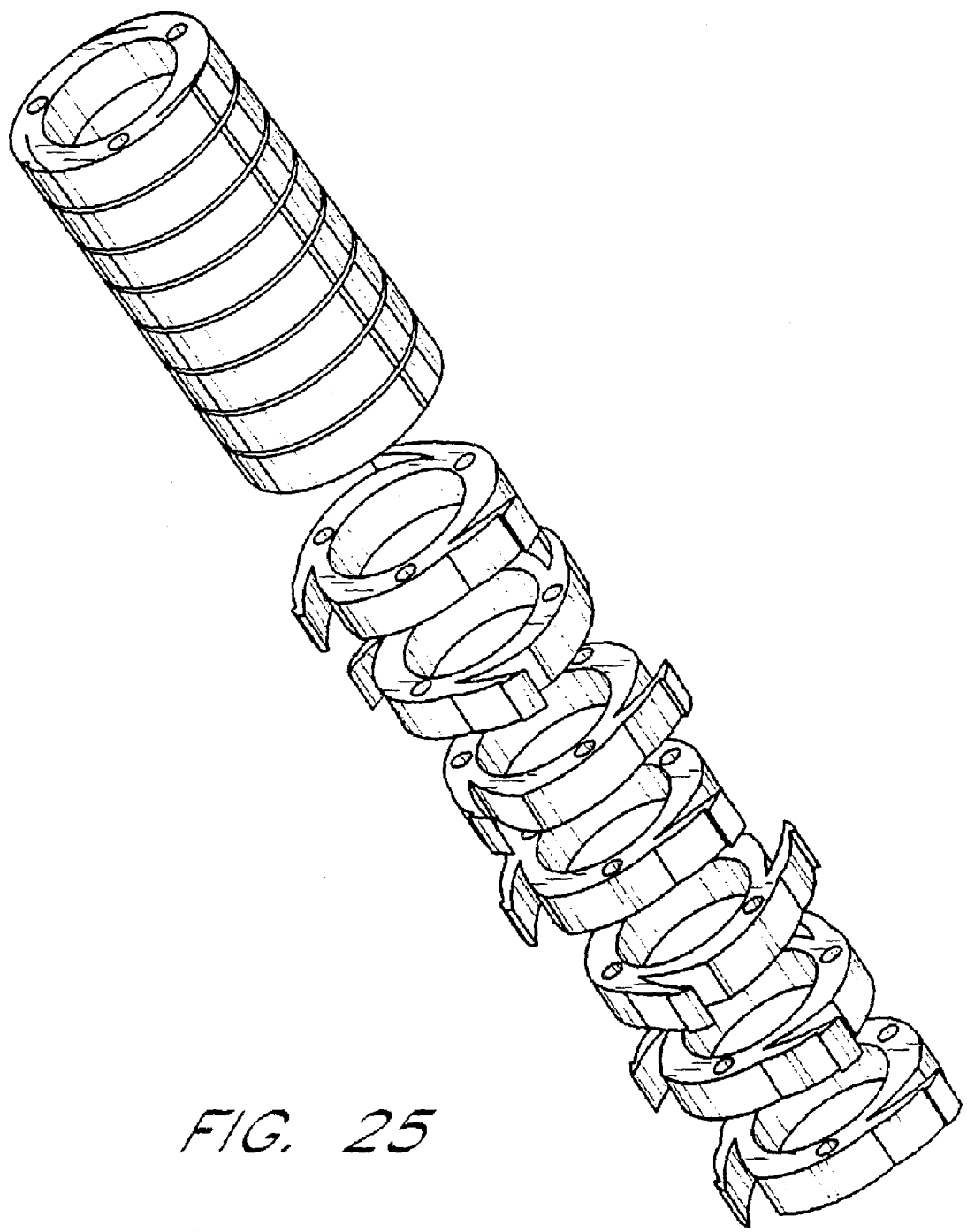
FIG. 25 is a perspective view of a bulkhead stent, with the rings of the stent in loaded and inserted configurations.

FIGS. 16–19 show one embodiment for deploying the bulkhead stent 50 into the myocardium MYO. As the delivery catheter 60 is retracted proximally from the myocardium MYO, the rings comprising the bulkhead stent 50 are deployed into the myocardium MYO. FIGS. 20 and 21 are enlarged views of FIGS. 18 and 19, showing the rings of the bulkhead stent 50 positioned within the myocardium MYO to form the passageway therethrough.

FIGS. 22–25 illustrate more particularly the structure and deployment of the rings comprising the bulkhead stent 50. As shown in FIG. 24, the bulkhead stent comprises a plurality of rings 64 that are initially loaded into the delivery catheter 60. While inside the lumen of the catheter 60, each ring 64 has a loaded configuration 64A, shown in FIGS. 22 and 25. After ejectment from the catheter 60, the ring 64 assumes an inserted configuration 64B, shown in FIGS. 23 and 25. Preferably, the inserted configuration of ring 64B includes a plurality of flanges 66 around the circumference of each ring 64, thereby providing a securement mechanism to anchor each ring 64 to the myocardium MYO. Each ring 64 transforms from its loaded configuration 64A to its inserted configuration 64B by virtue of being released from the catheter 60. Specifically, the catheter 60 acts as a restraint on each ring 64 to keep it in its loaded configuration 64A. Then, once the ring 64 is released from the catheter 60, the flanges 66 provided along the circumference of each ring 64 are allowed to extend outward to provide the securement mechanism.

Figure 26:
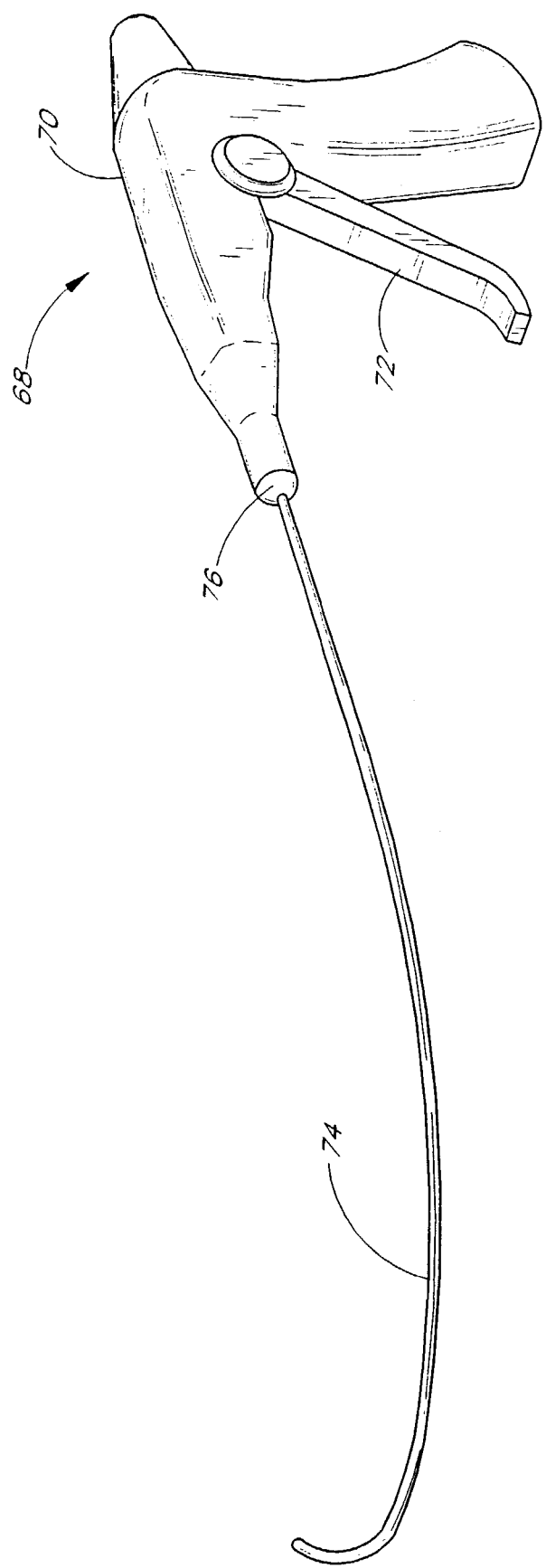
FIG. 26 is a perspective view of an inserter device used to insert a bulkhead stent.
Figure 27A:
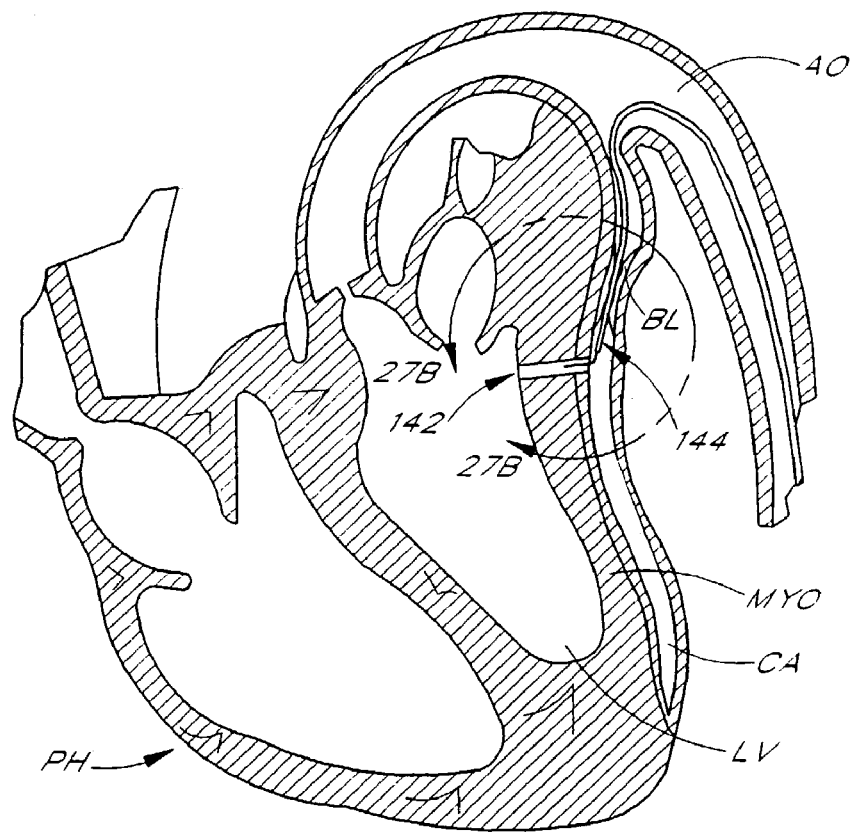
FIG. 27A is a schematic, cross-sectional view of the human heart, showing a catheter used to form a channel through the myocardium and into the left ventricle inserted into the coronary artery.
Figure 27B:
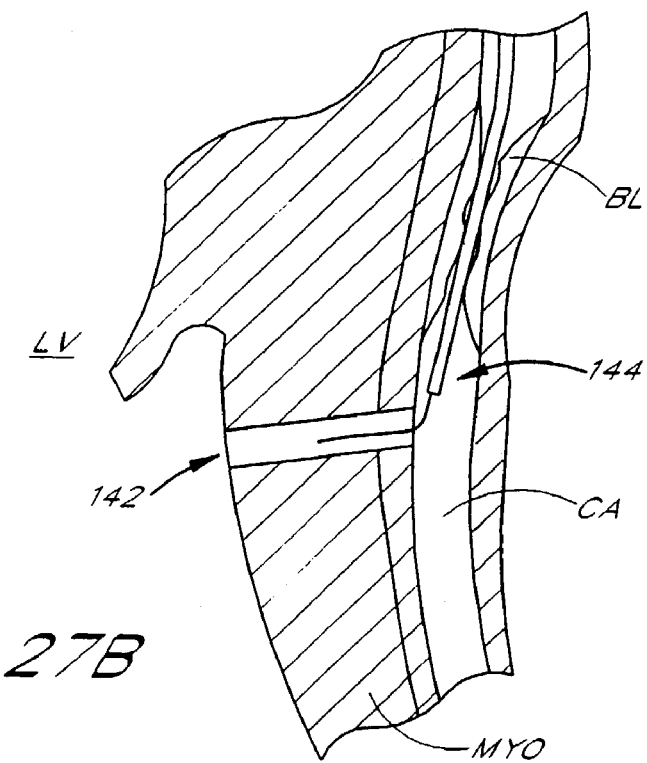
FIG. 27B is an enlarged view of the distal end of the catheter and the channel through the myocardium in FIG. 27A.

FIG. 26 illustrates an inserter device or handle 68 that may be used in deploying the bulkhead stent 50 into the myocardium. The inserter handle 68 preferably comprises a gun 70 with a trigger 72, and a wire 74 extending from a nozzle 76. The rings 64 (not shown) of the bulkhead stent 50 are preferably loaded onto the wire 74, and may be deployed into the myocardium preferably one at a time by pressing the trigger 72.

Figure 28:
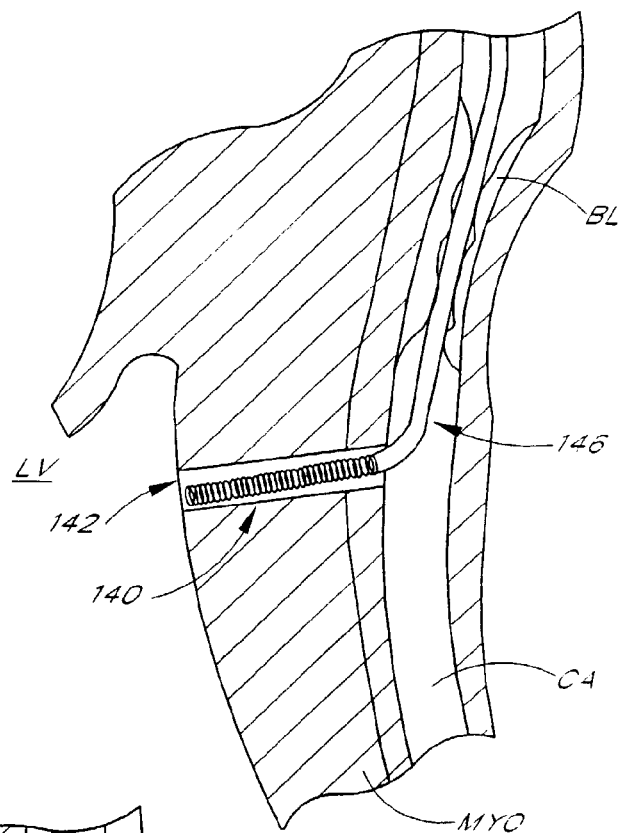
FIG. 28 is a schematic, cross-sectional view of a stent delivery catheter positioned inside the channel formed in the myocardium.
Figure 29:
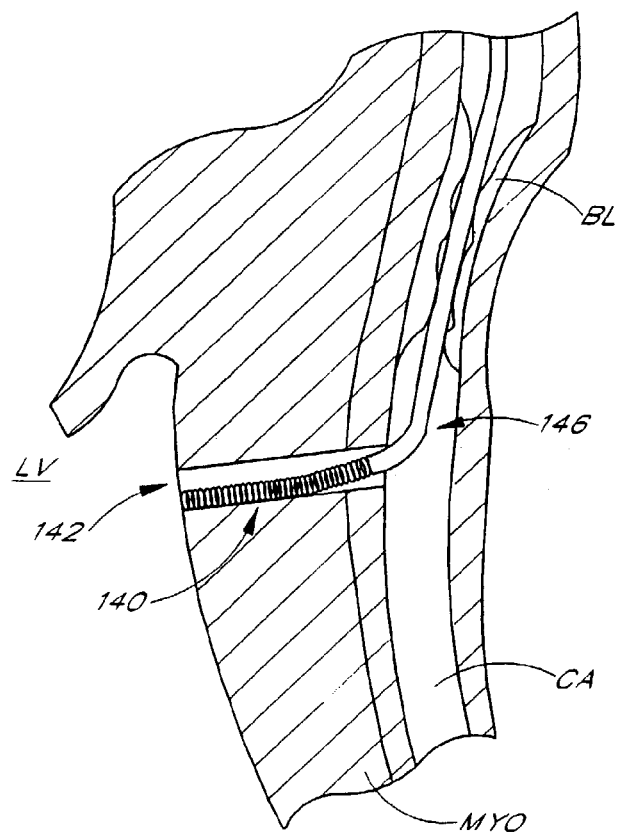
FIG. 29 is a schematic, partial cross-sectional view of a self-expanding spring stent being positioned in the channel formed in the myocardium.
Figure 30:
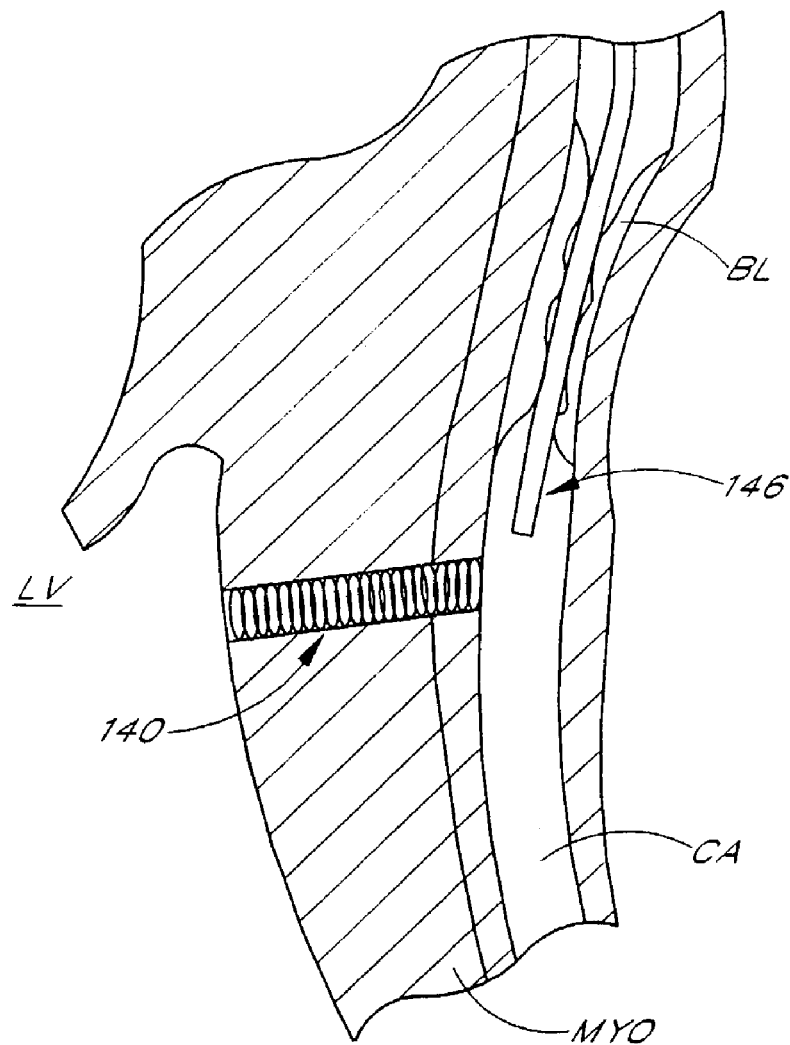
FIG. 30 is a schematic, partial cross-sectional view of the self-expanding stent deployed within the myocardium.

FIGS. 27–30 illustrate another embodiment of the present invention. Here, a self-expanding spring or screw stent 140 is delivered into the myocardium MYO. As illustrated in FIG. 27A, a channel 142 through the wall of the myocardium MYO is first created, as described above, using a device 144 delivered through the aorta AO and coronary artery CA. The channel 142 travels from the coronary artery CA through the myocardium MYO and into the left ventricle LV as shown in FIG. 27B. The distal end of the stent delivery catheter 146 bearing the stent 140 is then positioned within the channel 142, as shown in FIG. 28. Preferably, the position of the distal end of the delivery catheter 146 is checked radiographically, to ensure proper positioning. Next, as illustrated in FIG. 29, the self-expanding spring stent 140 is delivered into the channel 142 wall of the myocardium MYO. The stent 140 is cut such that it does not extend past the myocardium MYO and into either the left ventricle LV or the coronary artery CA. Again, the proper positioning and length of the stent 140 is preferably checked radiographically and any necessary adjustments made before the delivery catheter 146 is removed, as shown in FIG. 30.

Figure 31:
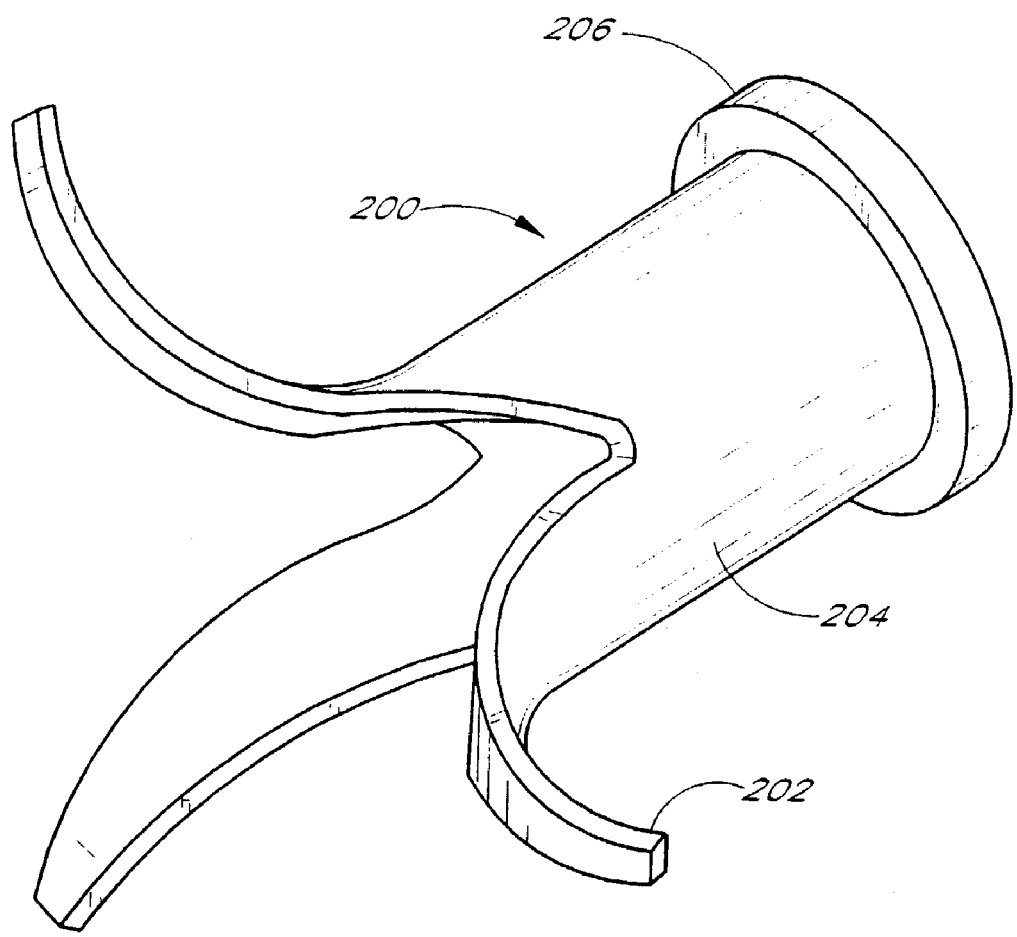
FIG. 31 is a perspective view of another embodiment of a stent having retention members which maintain the position of the stent.

FIG. 31 illustrates another embodiment of the stent 200 having retention members 202. The hollow stent body 204 is held in place in the heart wall by one or more retention members 202 which are deployed after the stent 200 is properly positioned, as described above. FIG. 31 shows the retention members 202 in their deployed position. A flange 206 acts to seal the opening in the coronary artery, while the retention members 202 reside in the myocardium, helping to anchor the stent 200 in place.

It should be appreciated that the stents described above, and particularly the bulkhead stent, are useful in other applications in addition to stenting the myocardium. For example, these stents may also serve as other types of coronary stents, arterial or venous stents, as well as billiary and esophageal stents.

The present vascular shunt provides significant improvements in the present treatment of blockages in the coronary artery. Although the invention has been described in its preferred embodiments in connection with the particular figures, it is not intended that this description should be limited in any way.

What is claimed is:

1. A method for treating a heart, the method comprising:
    delivering a conduit in a contracted configuration to a heart wall, the conduit including a plurality of units;
    expanding the conduit in a passage in the heart wall between a heart chamber and a coronary vessel; and
    sizing the conduit so that a first end of the conduit is positioned proximate the coronary vessel and a second end of the conduit is positioned proximate the heart chamber,
    wherein sizing the conduit includes adjusting a length of the conduit.

2. The method of claim 1, further comprising adjusting a position of the conduit within the heart wall.

3. The method of claim 1, wherein sizing the conduit includes cutting the conduit.

4. The method of claim 1, wherein delivering the plurality of units includes delivering the plurality of units in an aligned configuration.

5. The method of claim 1, wherein the plurality of units are connected.

6. The method of claim 5, wherein the plurality of units are connected by a wire.

7. The method of claim 5, wherein the plurality of units are interconnected.

8. The method of claim 1, wherein delivering the plurality of units includes delivering the plurality of units one at a time.

9. The method of claim 8, wherein delivering the plurality of units one at a time includes depressing a mechanism on a handle.

10. The method of claim 1, wherein the plurality of units comprise a plurality of ring-like elements.

11. The method of claim 10, wherein the ring-like elements are connected to each other.

12. The method of claim 10, wherein the ring-like elements are interconnected.

13. The method of claim 10, wherein the ring-like elements form a coil.

14. The method of claim 1, wherein delivering the plurality of units includes expanding the plurality of units from a delivered configuration within a delivery catheter to an expanded configuration in the heart wall.

15. The method of claim 1, wherein the coronary vessel is a coronary artery and the heart chamber is a left ventricle.

16. The method of claim 1, wherein the plurality of units includes at least one flange.

17. The method of claim 1, wherein the conduit is configured to place the heart chamber and the coronary vessel in flow communication with each other.

18. The method of claim 1, further comprising securing the conduit within the passage.

19. The method of claim 18, wherein securing the conduit includes attaching at least a portion of the conduit to the heart wall.

20. The method of claim 18, wherein securing the conduit includes attaching at least one of the plurality of units to the heart wall.

21. The method of claim 18, wherein securing the conduit includes deploying an attachment portion of the conduit within the passage.

22. The method of claim 1, further comprising delivering at least one agent to the heart wall via the conduit.

23. The method of claim 22, wherein the at least one agent is chosen from drugs, genes, angiogenesis factors, and growth factors.

24. A method for treating a heart, method comprising:
    delivering a conduit in a contracted configuration to a heart wall, the conduit including a plurality of units;
    expanding the conduit in a passage in the heart wall between a heart chamber and a coronary vessel; and
    sizing the conduit so that a first end of the conduit is positioned proximate the coronary vessel and a second end of the conduit is positioned proximate the heart chamber,
    wherein sizing the conduit includes shortening the conduit.

25. A method for treating a heart, the method comprising:
    delivering a conduit in a contracted configuration to a heart wall, the conduit including a plurality of units;
    expanding the conduit in a passage in the heart wall between a heart chamber and a coronary vessel;
    sizing the conduit so that a first end of the conduit is positioned proximate the coronary vessel and a second end of the conduit is positioned proximate the heart chamber; and
    adjusting a position of the conduit within the heart wall, wherein the adjusting the position is performed after the delivering of the conduit.

26. A method for treating a heart, the method comprising:
    delivering a conduit in a contracted configuration to a heart wall, the conduit including a plurality of units;
    expanding the conduit in a passage in the heart wall between a heart chamber and a coronary vessel; and
    sizing the conduit so that a first end of the conduit is positioned proximate the coronary vessel and a second end of the conduit is positioned proximate the heart chamber,
    wherein the plurality of units are connected by a suture.

27. A method for treating a heart, the method comprising:
    delivering a conduit in a contracted configuration to a heart wall, the conduit including a plurality of units;
    expanding the conduit in a passage in the heart wall between a heart chamber and a coronary vessel; and sizing the conduit so that a first end of the conduit is positioned proximate the coronary vessel and a second end of the conduit is positioned proximate the heart chamber, wherein the plurality of units comprise a plurality of ring-like elements, wherein the ring-like elements are separable from each other.

28. A method for treating a heart, the method comprising:

delivering a conduit in a contracted configuration to a heart wall, the conduit including a plurality of units;

expanding the conduit in a passage in the heart wall between a heart chamber and a coronary vessel; and sizing the conduit so that a first end of the conduit is positioned proximate the coronary vessel and a second end of the conduit is positioned proximate the heart chamber, wherein the plurality of units are not connected.

29. A method for treating a heart, the method comprising:

delivering a conduit in a contracted configuration to a heart wall, the conduit including a plurality of units;

expanding the conduit in a passage in the heart wall between a heart chamber and a coronary vessel; and sizing the conduit so that a first end of the conduit is positioned proximate the coronary vessel and a second end of the conduit is positioned proximate the heart chamber, wherein the plurality of units includes at least one flange, wherein delivering the plurality of units includes extending the at least one flange outward.

30. A method of treating a heart, the method comprising:

providing a plurality of units in a delivery device; and deploying each of the plurality of units one at a time in a passage in a heart wall between a heart chamber and a coronary vessel to form a conduit that is sized so that a first end of the conduit is positioned proximate the coronary vessel and a second end of the conduit is positioned proximate the heart chamber, wherein deploying the plurality of units includes expanding the plurality of units from a delivered configuration within the delivery device to an expanded configuration in the heart wall.

31. The method of claim 30, wherein deploying the plurality of units includes deploying the plurality of units in an aligned configuration.

32. The method of claim 30, wherein the plurality of units are connected.

33. The method of claim 32, wherein the plurality of units are connected by a wire.

34. The method of claim 30, wherein deploying the plurality of units one at a time includes depressing a mechanism on a handle of the delivery device.

35. The method of claim 30, wherein the plurality of units comprise a plurality of ring-like elements.

36. The method of claim 35, wherein the ring-like elements are connected to each other.

37. The method of claim 30, wherein the coronary vessel is a coronary artery and the heart chamber is a left ventricle.

38. The method of claim 30, wherein the plurality of units includes at least one flange.

39. The method of claim 30, wherein the conduit is configured to place the heart chamber and the coronary vessel in flow communication with each other.

40. The method of claim 30, further comprising securing the conduit within the passage.

41. The method of claim 40, wherein securing the conduit includes attaching at least a portion of the conduit to the heart wall.

42. The method of claim 40, wherein securing the conduit includes attaching at least one of the plurality of units to the heart wall.

43. The method of claim 40, wherein securing the conduit includes deploying an attachment portion of the conduit within the passage.

44. The method of claim 30, further comprising inserting the delivery device into the heart wall percutaneously.

45. The method of claim 30, further comprising inserting the delivery device into the heart wall over a wire.

46. The method of claim 30, wherein deploying the plurality of units includes retracting the delivery device from the heart wall.

47. The method of claim 30, wherein the delivery device includes a catheter.

48. The method of claim 30, further comprising delivering at least one agent to the heart wall via the plurality of units.

49. The method of claim 48, wherein the at least one agent is chosen from drugs, genes, angiogenesis factors, and growth factors.

50. A method of treating a heart, the method comprising:

providing a plurality of units in a delivery device; and deploying each of the plurality of units one at a time in a passage in a heart wall between a heart chamber and a coronary vessel to form a conduit that is sized so that a first end of the conduit is positioned proximate the coronary vessel and a second end of the conduit is positioned proximate the heart chamber, wherein the plurality of units are connected by a suture.

51. The method of claim 32, wherein the plurality of units are interconnected.

52. A method of treating a heart, the method comprising:

providing a plurality of units in a delivery device; and deploying each of the plurality of units one at a time in a passage in a heart wall between a heart chamber and a coronary vessel to form a conduit that is sized so that a first end of the conduit is positioned proximate the coronary vessel and a second end of the conduit is positioned proximate the heart chamber, wherein the plurality of units comprise a plurality of ring-like elements, wherein the ring-like elements are separable from each other.

53. A method of treating a heart, the method comprising:

providing a plurality of units in a delivery device; and deploying each of the plurality of units one at a time in a passage in a heart wall between a heart chamber and a coronary vessel to form a conduit that is sized so that a first end of the conduit is positioned proximate the coronary vessel and a second end of the conduit is positioned proximate the heart chamberm, wherein the plurality of units are not connected.

54. A method of treating a heart, the method comprising:

providing a plurality of units in a delivery device; and deploying each of the plurality of units one at a time in a passage in a heart wall between a heart chamber and a coronary vessel to form a conduit that is sized so that a first end of the conduit is positioned proximate the coronary vessel and a second end of the conduit is positioned proximate the heart chamber, wherein the plurality of units includes at least one flange, wherein deploying the plurality of units includes extending the at least one flange outward.

55. A method for treating a heart, the method comprising:
  providing a conduit comprising a plurality of unconnected units;
  delivering the conduit to a passage in a heart wall between a heart chamber and a coronary vessel; and
  sizing the conduit so that a first end of the conduit is positioned proximate the coronary vessel and a second end of the conduit is positioned proximate the heart chamber.

56. The method of claim 55, wherein delivering the conduit includes deploying the plurality of unconnected units in an aligned configuration.

57. The method of claim 55, wherein delivering the conduit includes depressing a mechanism on a handle of the delivery device.

58. The method of claim 55, wherein the plurality of unconnected units comprise a plurality of ring-like elements.

59. The method of claim 55, wherein delivering the conduit includes expanding the plurality of unconnected units from a delivered configuration within a delivery device to an expanded configuration in the heart wall.

60. The method of claim 55, wherein the coronary vessel is a coronary artery and the heart chamber is a left ventricle.

61. The method of claim 55, wherein the conduit includes at least one flange.

62. The method of claim 61, wherein delivering the conduit includes extending the at least one flange outward.

63. The method of claim 55, wherein the conduit is configured to place the heart chamber and the coronary vessel in flow communication with each other.

64. The method of claim 55, further comprising securing the conduit within the passage.

65. The method of claim 64, wherein securing the conduit includes attaching at least a portion of the conduit to the heart wall.

66. The method of claim 64, wherein securing the conduit includes attaching at least one of the plurality of unconnected units to the heart wall.

67. The method of claim 64, wherein securing the conduit includes deploying an attachment portion of the conduit within the passage.

68. The method of claim 55, further comprising delivering at least one agent to the heart wall via the conduit.

69. The method of claim 68, wherein the at least one agent is chosen from drugs, genes, angiogenesis factors, and growth factors.

* * * * *

UNITED STATES PATENT AND TRADEMARK OFFICE
CERTIFICATE OF CORRECTION

PATENT NO.        : 7,101,402 B2                                          Page 1 of 1
APPLICATION NO.   : 10/456488
DATED             : September 5, 2006
INVENTOR(S)       : David Phelps et al.

It is certified that error appears in the above-identified patent and that said Letters Patent is hereby corrected as shown below:

Claim 24, column 10, line 28, "heart, method" should read --heart, the method--;

Claim 53, column 12, line 55, "chamberm" should read -- chamber--.

Signed and Sealed this

Fifth Day of December, 2006

JON W. DUDAS
*Director of the United States Patent and Trademark Office*